United States Patent
Hu

(10) Patent No.: US 12,312,346 B2
(45) Date of Patent: May 27, 2025

(54) PYRIDOPYRIMIDINE COMPOUNDS AND METHODS OF THEIR USE

(71) Applicant: Tufts Medical Center, Inc., Boston, MA (US)

(72) Inventor: Miaofen G. Hu, Boston, MA (US)

(73) Assignee: Tufts Medical Center, Inc., Boston, MA (US)

( * ) Notice: Subject to any disclaimer, the term of this patent is extended or adjusted under 35 U.S.C. 154(b) by 1105 days.

(21) Appl. No.: 17/256,318

(22) PCT Filed: Jun. 27, 2019

(86) PCT No.: PCT/US2019/039471
§ 371 (c)(1),
(2) Date: Dec. 28, 2020

(87) PCT Pub. No.: WO2020/006210
PCT Pub. Date: Jan. 2, 2020

(65) Prior Publication Data
US 2021/0261547 A1 Aug. 26, 2021

Related U.S. Application Data

(60) Provisional application No. 62/690,450, filed on Jun. 27, 2018.

(51) Int. Cl.
 *C07D 471/04* (2006.01)
 *A61P 35/00* (2006.01)
(52) U.S. Cl.
 CPC ............ *C07D 471/04* (2013.01); *A61P 35/00* (2018.01)
(58) Field of Classification Search
 CPC ........... C07D 471/04; A61P 35/00; A61P 3/00
 USPC ....................................... 514/252
 See application file for complete search history.

(56) References Cited

U.S. PATENT DOCUMENTS

| | | | |
|---|---|---|---|
| 6,696,566 B2 | 2/2004 | Chen et al. | |
| 2004/0224958 A1* | 11/2004 | Booth | A61P 21/02 514/264.11 |
| 2005/0182078 A1* | 8/2005 | Barvian | A61P 35/00 514/264.11 |

FOREIGN PATENT DOCUMENTS

| | | | | |
|---|---|---|---|---|
| WO | WO-01/55148 A1 | 8/2001 | | |
| WO | WO-2008047307 A1 * | 4/2008 | ........... | A61K 31/519 |
| WO | WO-2016/015597 A1 | 2/2016 | | |
| WO | WO-2016015598 A1 * | 2/2016 | ........... | A61K 31/519 |

OTHER PUBLICATIONS

Malínková et al. Expert Opinion on Therapeutic Patents, 2015, 25:9, pp. 953-970, DOI: 10.1517/13543776.2015.1045414, "Cyclin-dependent kinase inhibitors for cancer therapy: a patent review (2009-2014)" (Year: 2015).*
International Preliminary Report on Patentability mailed Jan. 7, 2021 for PCT International Application No. PCT/US2019/039471, Hu, M. "Pyridopyrimidine Compounds and Methods of their use," filed Jun. 27, 2019 (8 pages).
International Search Report and Written Opinion mailed Sep. 13, 2019 for PCT International Application No. PCT/US2019/039471, Hu, M., "Pyridopyrimidine Compounds and Methods of Their Use," filed Jun. 27, 2019 (12 pages).

* cited by examiner

*Primary Examiner* — Jared Barsky
*Assistant Examiner* — Liyuan Mou
(74) *Attorney, Agent, or Firm* — Clark & Elbing LLP

(57) ABSTRACT

Disclosed are compounds of formula (I) or a pharmaceutically acceptable salt thereof, where X is O or S; $R^1$ is hydrogen, an optionally substituted $C_{1-6}$ alkyl, or an optionally substituted $C_{3-8}$ cycloalkyl; each of $R^2$, $R^3$, and $R^4$ is independently hydrogen, halo, or an optionally substituted $C_{1-6}$ alkyl; $R^5$ is a substituted $C_3$ heteroaryl; and $R^6$ is hydrogen or an optionally substituted $C_{1-6}$ alkyl. Also disclosed are pharmaceutical compositions and methods of their use.

2 Claims, 23 Drawing Sheets

WAT inducers

BAT inducers

PYRIDOPYRIMIDINE COMPOUNDS AND METHODS OF THEIR USE

FIELD OF THE INVENTION

The invention provides compounds, pharmaceutical compositions containing them, and methods of their use, e.g., for the treatment of cancer (e.g., leukemia, lung cancer, or brain tumor) or metabolic diseases (e.g., obesity).

BACKGROUND

Cyclin-dependent kinases 4 and 6 (CDK4 and CDK6) are important cellular enzymes that perform essential functions in regulating cell division and proliferation. In particular, cyclin-dependent kinases 4/6 (CDKs 4/6) play a role in the regulation of the cell cycle in early G1 phase. Proliferative stimuli induce the expression of D-type cyclins, which assemble with CDK4 and CDK6. This results in the activation of CDKs 4/6 and the nuclear import of their holoenzymes, where they collaborate with cyclin E-CDK2 to promote cell division by phosphorylation of pRB, as well as the pRB-related family proteins p107 and p1301. Hyperphosphorylation of pRB results in activation or de-repression of E2F-dependent promoters and the transcription of genes required for S-phase entry. Thus, D-cyclin-CDK4/6 complexes are believed to play a catalytic role in the G1-S transition by negatively regulating pRB function.

Consistent with the idea that CDK4 and CDK6 may differentially impact proliferation in a cell-type dependent manner, CDK6 is overexpressed in human T-cell lymphoblastic lymphoma/leukemia, and the CDK6 locus is amplified in 25% of peripheral T-cell lymphomas. CDK6 also plays a role in the development of lymphoid malignancy in E47-deficient T-cell lineages. Alternatively, aberration in cell cycle regulation, especially sustained CDK4/6 activation, is a common theme in the majority of human cancers including T-cell acute lymphoblastic leukemia (T-ALL). For example, 70% of T-ALL patients have deletion mutations of the tumor suppressors p16$^{INK4A}$ and p14$^{ARF}$. In contrast, CDK4 is believed to be specifically mutated in human melanomas and over-expressed in a significant fraction of human breast cancers. Moreover, CDK6 was shown to have a specific role in differentiation of certain cell types such as in astrocytes, osteoblasts, and murine erythroid leukemia cells. This function is apparently not shared with CDK4.

CDK6 kinase activity is believed to be critical to induction of Notch1-mediated T-ALL in a mouse model. Donor cells lacking the CDK6 protein or its kinase activity, while expressing intact CDK4, were observed to be resistant to transformation by activated Notch1 as a consequence of reduced proliferation and increased apoptosis. Re-expression of CDK6 in CDK6-deficient or kinase-dead stem cells rescues this defect, arguing for a cell-autonomous effect of CDK6 downstream of NOTCH1 in leukemogenesis. In complementary studies, deletion of cyclin D3 (an activating partner of CDK4/6) or treatment with palbociclib, an inhibitor of CDK4/6, was observed to induce cell cycle arrest and apoptosis in Notch1-induced mouse T-ALLs and prolonged survival of mice having this leukemia. Tests of the response of human T-ALL cell lines with constitutively active Notch1 mutations to palbociclib or Cdk6-shRNAs have confirmed applicability of the CDK4/6 inhibition as a therapeutic approach for human leukemias. In these tests, palbociclib or CDK6-shRNAs treatment inhibited cell proliferation and induced apoptosis, recapitulating the effects seen in the mouse models. Taken together, these data indicate that CDK6, as a downstream effector of Notch1, is required for initiation and maintenance of Notch1-induced T-ALL.

Recent evidence also indicates that AKT-activating mutations are frequently found in many types of human T-ALL and murine T-cell tumors. Over-expression of an active form of AKT (MyrAkt1) in WT T-cell progenitors induces T-cell lymphoma accompanied with increased level of CD44. However, CDK6-deficient mice are resistant to MyrAkt1-induced T-cell hematopoietic malignancies, in support of CDK6 being a major oncogenic driver downstream of AKT, with higher expression of CD25 and lower expression of CD44. Thus, CDK6 is also required for T-cell tumorigenesis in an AKT-dependent pathway.

CDK6 is thus believed to act as a common downstream target of Notch and PI3K-AKT signaling pathways in T-cell tumorigenesis, which indicates that CDK6 inhibitors may be useful in the treatment of cancer (e.g., T-ALLs). Indeed, more than half of T-ALLs have activating NOTCH1 mutations or abnormalities in the PTEN-AKT pathways.

In rodents and humans, fat is deposited as energy storage in white adipose tissue (WAT), whereas fat is consumed to produce heat in the mitochondria-rich brown adipose tissues (BAT). As a thermogenic tissue, inducible-brown adipocytes (also called beige cells) are found sporadically in WAT of adult animals with similar features as classical brown adipocytes but originate from a non-myf5-derived cell lineage, likely developed from the progenitor cells residing in the stromal vascular fraction (SVF) of white adipose depots. Importantly, the activation of beige cells is associated with protection against obesity and metabolic diseases in rodent models and correlated with leanness in humans.

CDK6 plays an important role in proliferation and differentiation. To address the role of CDK6 in development and tumorigenesis, we have produced both knockout (CDK6$^{-/-}$ or KO) and knock-in mice. The knock-in mutants include CDK6R31C (R31C), a hyper-active, inhibitor-resistant kinase that cannot interact with INK4 family inhibitor proteins, and a catalytically inactive kinase, CDK6K43M (K43M). The R31C mutant mimics hyperactivation of CDK6 in tumor/disease cells, whereas the catalytic inactive K43M mutant model pharmacological inhibition of kinase activity.

Employing Cdk6 mutant mice, we have found that mice lacking the CDK6 protein (CDK6$^{-/-}$) or its kinase domain (K43M) exhibit same phenotypes such as significantly reduced fat pad mass in subcutaneous adipose tissue (SAT) and visceral adipose tissues (VAT), increased WAT browning in SAT, enhanced energy expenditure, more resistant to high fat diet (HFD)-induced obesity, better glucose tolerance, and improved insulin sensitivity. Re-expression of CDK6 in mature adipocytes reverses the phenotypes observed in CDK6$^{-/-}$ mice.

There is a need for new therapeutic approaches for cancer and metabolic diseases, including obesity.

SUMMARY OF THE INVENTION

The invention provides compounds of formula (I):

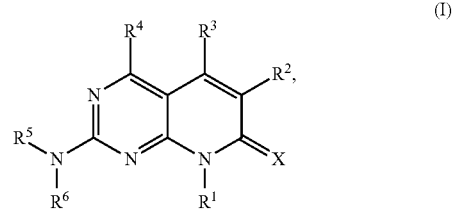

or pharmaceutically acceptable salts thereof, wherein X is O or S; $R^1$ is hydrogen, an optionally substituted $C_{1-6}$ alkyl, or an optionally substituted $C_{3-8}$ cycloalkyl; each of $R^2$, $R^3$, and $R^4$ is independently hydrogen, halo, or an optionally substituted $C_{1-6}$ alkyl (e.g., optionally substituted $C_{1-2}$ alkyl); $R^5$ is a substituted $C_3$ heteroaryl; and $R^6$ is hydrogen or an optionally substituted $C_{1-6}$ alkyl.

In some embodiments, X is O; $R^1$ is hydrogen; $R^2$ is an optionally substituted $C_{1-6}$ alkyl or $R^2$ is an optionally substituted $C_{1-6}$ alkanoyl (e.g., $C_{1-2}$ alkanoyl); $R^3$ is an optionally substituted $C_{1-6}$ alkyl (e.g., methyl); $R^4$ is hydrogen; and/or $R^5$ is a substituted thiazolyl or substituted oxazolyl; $R^5$ is thiazolyl or oxazolyl substituted with an optionally substituted $C_{1-9}$ heterocyclyl $C_{1-6}$ alkyl; or $R^5$ is a group of formula:

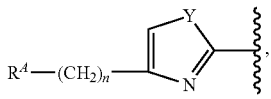

wherein n is an integer from 0 to 6; Y is S or O; and $R^A$ is an optionally substituted $C_{1-9}$ heterocyclyl (e.g., substituted $C_4$ heterocyclyl). In some embodiments, Y is S; n is 1; $R^A$ is N-piperazinyl; and/or $R^6$ is hydrogen.

The invention further provides a compound of the following structure:

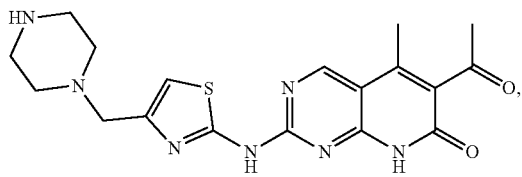 [SMILES: CC(=O)c1c(C)c2cnc(Nc3nc(CN4CCNCC4)cs3)nc2[nH]c1=O]

or a pharmaceutically acceptable salt thereof.

Also, the invention provides pharmaceutical compositions including a compound as described herein and a pharmaceutically acceptable excipient.

Further, the invention provides methods of treating a subject (e.g., a human subject) having a cancer (e.g., leukemia, lung cancer, breast cancer, brain tumor, cervical cancer, or pancreatic cancer), the methods including administering to the subject in need thereof an effective amount of a compound or pharmaceutical composition as described herein.

In addition, the invention provides methods of treating a subject (e.g., a human subject) having a metabolic disease (e.g., obesity, type II diabetes, metabolic syndrome, elevated blood pressure, a cardiovascular disease, elevated fasting plasma glucose, or a high level of serum triglycerides), the method including administering to the subject in need thereof an effective amount of a compound or pharmaceutical composition as described herein.

The invention also includes methods of inducing cell death in a cancer cell (e.g., a leukemic cell, a cervical cancer cell, a lung cancer cell, a brain tumor cell, a breast cancer cell, or a pancreatic cancer cell), the methods including contacting the cancer cell of a compound or pharmaceutical composition as described herein.

Definitions

The term "acyl," as used herein, represents a chemical substituent of formula —C(O)—R, where R is alkyl, aryl, arylalkyl, cycloalkyl, heterocyclyl, heterocyclyl alkyl, heteroaryl, or heteroaryl alkyl. An optionally substituted acyl is an acyl that is optionally substituted as described herein for each group R.

The term "acyloxy," as used herein, represents a chemical substituent of formula —OR, where R is acyl. An optionally substituted acyloxy is an acyloxy that is optionally substituted as described herein for acyl.

The term "alkanoyl," as used herein, represents a chemical substituent of formula —C(O)—R, where R is alkyl. An optionally substituted alkanoyl is an alkanoyl that is optionally substituted as described herein for alkyl.

The term "alkoxy," as used herein, represents a chemical substituent of formula —OR, where R is a $C_{1-6}$ alkyl group, unless otherwise specified. An optionally substituted alkoxy is an alkoxy group that is optionally substituted as defined herein for alkyl.

The term "alkyl," as used herein, refers to an acyclic straight or branched chain saturated hydrocarbon group, which, when unsubstituted, has from 1 to 12 carbons, unless otherwise specified. In certain preferred embodiments, unsubstituted alkyl has from 1 to 6 carbons. Alkyl groups are exemplified by methyl; ethyl; n- and iso-propyl; n-, sec-, iso- and tert-butyl; neopentyl, and the like, and may be optionally substituted, valency permitting, with one, two, three, or, in the case of alkyl groups of two carbons or more, four or more substituents independently selected from the group consisting of: alkoxy; acyloxy; amino; aryl; aryloxy; azido; cycloalkyl; cycloalkoxy; halo; heterocyclyl; heteroaryl; heterocyclylalkyl; heteroarylalkyl; heterocyclyloxy; heteroaryloxy; hydroxy; nitro; thiol; silyl; cyano; =O; =S; and =NR', where R' is H, alkyl, aryl, or heterocyclyl. In some embodiments, two substituents combine to form a group -L-CO—R, where L is a bond or optionally substituted $C_{1-11}$ alkylene, and R is hydroxyl or alkoxy. Each of the substituents may itself be unsubstituted or, valency permitting, substituted with unsubstituted substituent(s) defined herein for each respective group.

The term "aryl," as used herein, represents a mono-, bicyclic, or multicyclic carbocyclic ring system having one or two aromatic rings. Aryl group may include from 6 to 10 carbon atoms. All atoms within an unsubstituted carbocyclic aryl group are carbon atoms. Non-limiting examples of carbocyclic aryl groups include phenyl, naphthyl, 1,2-dihydronaphthyl, 1,2,3,4-tetrahydronaphthyl, fluorenyl, indanyl, indenyl, etc. The aryl group may be unsubstituted or substituted with one, two, three, four, or five substituents independently selected from the group consisting of: alkyl; alkoxy; acyloxy; amino; aryl; aryloxy; azido; cycloalkyl; cycloalkoxy; halo; heterocyclyl; heteroaryl; heterocyclylalkyl; heteroarylalkyl; heterocyclyloxy; heteroaryloxy; hydroxy; nitro; thiol; silyl; and cyano. Each of the substituents may itself be unsubstituted or substituted with unsubstituted substituent(s) defined herein for each respective group.

The term "aryl alkyl," as used herein, represents an alkyl group substituted with an aryl group. The aryl and alkyl portions may be optionally substituted as the individual groups as described herein.

The term "aryloxy," as used herein, represents a group —OR, where R is aryl. Aryloxy may be an optionally substituted aryloxy. An optionally substituted aryloxy is aryloxy that is optionally substituted as described herein for aryl.

The expression "$C_{x-y}$," as used herein, indicates that the group, the name of which immediately follows the expression, when unsubstituted, contains a total of from x to y carbon atoms. If the group is a composite group (e.g., aryl alkyl), $C_{x-y}$ indicates that the portion, the name of which immediately follows the expression, when unsubstituted, contains a total of from x to y carbon atoms. For example, ($C_{6-10}$-aryl)-$C_{1-6}$-alkyl is a group, in which the aryl portion, when unsubstituted, contains a total of from 6 to 10 carbon atoms, and the alkyl portion, when unsubstituted, contains a total of from 1 to 6 carbon atoms.

The term "CDK4," as used herein, refers to cyclin-dependent kinase 4 protein or to a gene, pre-mRNA, or mRNA encoding cyclin-dependent kinase 4 protein. Preferably, CDK4 is a human CDK4 (hCDK4). An exemplary protein sequence for hCDK4 is found at NCBI Reference Sequence: NP_000066.1.

The term "CDK6," as used herein, refers to cyclin-dependent kinase 6 protein or to a gene, pre-mRNA, or mRNA encoding cyclin-dependent kinase 6 protein. Preferably, CDK6 is a human CDK6 (hCDK6). An exemplary protein sequence for hCDK6 is found at NCBI Reference Sequence: NP_001250.1.

The term "CDK6 inhibitor," as used herein, represents a compound that upon contacting a cell (e.g., mouse WT-MEF cell) expressing CDK6 inhibits the cell proliferation with IC50 of about 1 µM or less (e.g., about 200 µM or less, about 10 µM or less, about 5 µM or less). The CDK6 inhibitor IC50 in a mouse WT-MEF cell proliferation assay may be at least 10 pM (e.g., at least 100 pM or at least 1 nM). Preferably, the CDK6 inhibitor IC50 in a mouse WT-MEF cell proliferation assay is about 1 nM to about 10 µM (e.g., about 10 nM to about 5 µM, about 10 nM to about 2 µM, or about 100 nM to about 2 µM).

The term "cycloalkyl," as used herein, refers to a cyclic alkyl group having from three to ten carbons (e.g., a $C_3$-$C_{10}$ cycloalkyl), unless otherwise specified. Cycloalkyl groups may be monocyclic or bicyclic. Bicyclic cycloalkyl groups may be of bicyclo[p.q.0]alkyl type, in which each of p and q is, independently, 1, 2, 3, 4, 5, 6, or 7, provided that the sum of p and q is 2, 3, 4, 5, 6, 7, or 8. Alternatively, bicyclic cycloalkyl groups may include bridged cycloalkyl structures, e.g., bicyclo[p.q.r]alkyl, in which r is 1, 2, or 3, each of p and q is, independently, 1, 2, 3, 4, 5, or 6, provided that the sum of p, q, and r is 3, 4, 5, 6, 7, or 8. The cycloalkyl group may be a spirocyclic group, e.g., spiro[p.q]alkyl, in which each of p and q is, independently, 2, 3, 4, 5, 6, or 7, provided that the sum of p and q is 4, 5, 6, 7, 8, or 9. Non-limiting examples of cycloalkyl include cyclopropyl, cyclobutyl, cyclopentyl, cyclohexyl, cycloheptyl, 1-bicyclo [2.2.1.]heptyl, 2-bicyclo[2.2.1.]heptyl, 5-bicyclo[2.2.1.]heptyl, 7-bicyclo[2.2.1.]heptyl, and decalinyl. The cycloalkyl group may be unsubstituted or substituted (e.g., optionally substituted cycloalkyl) with one, two, three, four, or five substituents independently selected from the group consisting of: alkyl; alkoxy; acyloxy; amino; aryl; aryloxy; azido; cycloalkyl; cycloalkoxy; halo; heterocyclyl; heteroaryl; heterocyclylalkyl; heteroarylalkyl; heterocyclyloxy; heteroaryloxy; hydroxy; nitro; thiol; silyl; cyano; =O; =S; =NR', where R' is H, alkyl, aryl, or heterocyclyl. Each of the substituents may itself be unsubstituted or substituted with unsubstituted substituent(s) defined herein for each respective group.

The term "cycloalkoxy," as used herein, represents a group —OR, where R is cycloalkyl. Cycloalkoxy may be an optionally substituted cycloalkoxy. An optionally substituted cycloalkoxy is cycloalkoxy that is optionally substituted as described herein for cycloalkyl.

The term "halo," as used herein, represents a halogen selected from bromine, chlorine, iodine, and fluorine.

The term "heteroaryl," as used herein, represents a monocyclic 5-, 6-, 7-, or 8-membered ring system, or a fused or bridging bicyclic, tricyclic, or tetracyclic ring system; the ring system contains one, two, three, or four heteroatoms independently selected from the group consisting of nitrogen, oxygen, and sulfur; and at least one of the rings is an aromatic ring. Non-limiting examples of heteroaryl groups include benzimidazolyl, benzofuryl, benzothiazolyl, benzothienyl, benzoxazolyl, furyl, imidazolyl, indolyl, isoindazolyl, isoquinolinyl, isothiazolyl, isothiazolyl, isoxazolyl, oxadiazolyl, oxazolyl, purinyl, pyrrolyl, pyridinyl, pyrazinyl, pyrimidinyl, quinazolinyl, quinolinyl, thiadiazolyl (e.g., 1,3,4-thiadiazole), thiazolyl, thienyl, triazolyl, tetrazolyl, dihydroindolyl, tetrahydroquinolyl, tetrahydroisoquinolyl, etc. The term bicyclic, tricyclic, and tetracyclic heteroaryls include at least one ring having at least one heteroatom as described above and at least one aromatic ring. For example, a ring having at least one heteroatom may be fused to one, two, or three carbocyclic rings, e.g., an aryl ring, a cyclohexane ring, a cyclohexene ring, a cyclopentane ring, a cyclopentane ring, or another monocyclic heterocyclic ring. Examples of fused heteroaryls include 1,2,3,5,8,8a-hexahydroindolizine; 2,3-dihydrobenzofuran; 2,3-dihydroindole; and 2,3-dihydrobenzothiophene. Heteroaryl may be optionally substituted with one, two, three, four, or five substituents independently selected from the group consisting of: alkyl; alkoxy; acyloxy; aryloxy; amino; arylalkoxy; cycloalkyl; cycloalkoxy; halogen; heterocyclyl; heterocyclyl alkyl; heteroaryl; heteroaryl alkyl; heterocyclyloxy; heteroaryloxy; hydroxyl; nitro; thiol; cyano; =O; —NR$_2$, where each R is independently hydrogen, alkyl, acyl, aryl, arylalkyl, cycloalkyl, heterocyclyl, or heteroaryl; —COOR$^A$, where R$^A$ is hydrogen, alkyl, aryl, arylalkyl, cycloalkyl, heterocyclyl, or heteroaryl; and —CON(R$^B$)$_2$, where each R$^B$ is independently hydrogen, alkyl, aryl, arylalkyl, cycloalkyl, heterocyclyl, or heteroaryl. Each of the substituents may itself be unsubstituted or substituted with unsubstituted substituent(s) defined herein for each respective group.

The term "heteroaryloxy," as used herein, refers to a structure —OR, in which R is heteroaryl. Heteroaryloxy can be optionally substituted as defined for heteroaryl.

The term "heterocyclyl," as used herein, represents a monocyclic, bicyclic, tricyclic, or tetracyclic non-aromatic ring system having fused or bridging 4-, 5-, 6-, 7-, or 8-membered rings, unless otherwise specified, the ring system containing one, two, three, or four heteroatoms independently selected from the group consisting of nitrogen, oxygen, and sulfur. Non-aromatic 5-membered heterocyclyl has zero or one double bonds, non-aromatic 6- and 7-membered heterocyclyl groups have zero to two double bonds, and non-aromatic 8-membered heterocyclyl groups have zero to two double bonds and/or zero or one carbon-carbon triple bond. Heterocyclyl groups have a carbon count of 1 to 16 carbon atoms unless otherwise specified. Certain heterocyclyl groups may have a carbon count up to 9 carbon atoms. Non-aromatic heterocyclyl groups include pyrrolinyl, pyrrolidinyl, pyrazolinyl, pyrazolidinyl, imidazolinyl, imidazolidinyl, piperidinyl, homopiperidinyl, piperazinyl, pyridazinyl, oxazolidinyl, isoxazolidinyl, morpholinyl, thiomorpholinyl, thiazolidinyl, isothiazolidinyl, thiazolidinyl, tetrahydrofuranyl, dihydrofuranyl, tetrahydrothienyl, dihydrothienyl, pyranyl, dihydropyranyl, dithiazolyl, etc. The term "heterocyclyl" also represents a heterocyclic compound having a bridged multicyclic structure in which one or more carbons and/or heteroatoms bridges two non-adjacent members of a monocyclic ring, e.g., quinuclidine, tropanes, or diaza-bicyclo[2.2.2]octane. The term "heterocyclyl" includes bicyclic, tricyclic, and tetracyclic groups in which any of the above heterocyclic rings is fused to one, two, or three carbocyclic rings, e.g., a cyclohexane ring, a cyclohexene ring, a cyclopentane ring, a cyclopentane ring, or another heterocyclic ring. Examples of fused heterocyclys include 1,2,3,5,8,8a-hexahydroindolizine; 2,3-dihydrobenzofuran; 2,3-dihydroindole; and 2,3-dihydrobenzothiophene. The heterocyclyl group may be unsubstituted or substituted with one, two, three, four or five substituents independently selected from the group consisting of: alkyl; alkoxy; acyloxy; aryloxy; amino; arylalkoxy; cycloalkyl; cycloalkoxy; halogen; heterocyclyl; heterocyclyl alkyl; heteroaryl; heteroaryl alkyl; heterocyclyloxy; heteroaryloxy; hydroxyl; nitro; thiol; cyano; =O; =S; —NR$_2$, where each R is independently hydrogen, alkyl, acyl, aryl, arylalkyl, cycloalkyl, heterocyclyl, or heteroaryl; —COOR$^A$, where R$^A$ is hydrogen, alkyl, aryl, arylalkyl, cycloalkyl, heterocyclyl, or heteroaryl; and —CON(R$^B$)$_2$, where each R$^B$ is independently hydrogen, alkyl, aryl, arylalkyl, cycloalkyl, heterocyclyl, or heteroaryl.

The term "heterocyclyl alkyl," as used herein, represents an alkyl group substituted with a heterocyclyl group. The heterocyclyl and alkyl portions of an optionally substituted heterocyclyl alkyl are optionally substituted as described for heterocyclyl and alkyl, respectively.

The term "heterocyclyloxy," as used herein, refers to a structure —OR, in which R is heterocyclyl. Heterocyclyloxy can be optionally substituted as described for heterocyclyl.

The terms "hydroxyl" and "hydroxy," as used interchangeably herein, represent —OH.

The term "oxo," as used herein, represents a divalent oxygen atom (e.g., the structure of oxo may be shown as =O).

The term "pharmaceutically acceptable," as used herein, refers to those compounds, materials, compositions, and/or dosage forms, which are suitable for contact with the tissues of an individual (e.g., a human), without excessive toxicity, irritation, allergic response and other problem complications commensurate with a reasonable benefit/risk ratio.

The phrase "pharmaceutically acceptable salt," as used herein, includes, for example, salts formed from an acid and a basic nitrogen group of, e.g., a compound as described herein (e.g., GD). Examples of such salts include acid addition salts and base addition salts, such as inorganic acid salts or organic acid salts (e.g., hydrochloric acid salt, sulfuric acid salt, citrate, hydrobromic acid salt, hydroiodic acid salt, nitric acid salt, bisulfate, phosphoric acid salt, super phosphoric acid salt, isonicotinic acid salt, acetic acid salt, lactic acid salt, salicylic acid salt, tartaric acid salt, pantothenic acid salt, ascorbic acid salt, succinic acid salt, maleic acid salt, fumaric acid salt, gluconic acid salt, saccharinic acid salt, formic acid salt, benzoic acid salt, glutaminic acid salt, methanesulfonic acid salt, ethanesulfonic acid salt, benzenesulfonic acid salt, p-toluenesulfonic acid salt, pamoic acid salt (pamoate)), as well as salts of aluminum, calcium, lithium, magnesium, calcium, sodium, zinc, and diethanolamine.

The term "protecting group," as used herein, represents a group intended to protect a hydroxy, an amino, or a carbonyl from participating in one or more undesirable reactions during chemical synthesis. The term "O-protecting group," as used herein, represents a group intended to protect a hydroxy or carbonyl group from participating in one or more undesirable reactions during chemical synthesis. The term "N-protecting group," as used herein, represents a group intended to protect a nitrogen containing (e.g., an amino or hydrazine) group from participating in one or more undesirable reactions during chemical synthesis. Commonly used O- and N-protecting groups are disclosed in Greene, "Protective Groups in Organic Synthesis," 3$^{rd}$ Edition (John Wiley & Sons, New York, 1999), which is incorporated herein by reference. Exemplary O- and N-protecting groups include alkanoyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl.

Exemplary O-protecting groups for protecting carbonyl containing groups include, but are not limited to: acetals, acylals, 1,3-dithianes, 1,3-dioxanes, 1,3-dioxolanes, and 1,3-dithiolanes.

Other O-protecting groups include, but are not limited to: substituted alkyl, aryl, and aryl-alkyl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl)ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenylmethylsilyl); carbonates (e.g., methyl, methoxymethyl, 9-fluorenylmethyl; ethyl; 2,2,2-trichloroethyl; 2-(trimethylsilyl)ethyl; vinyl, allyl, nitrophenyl; benzyl; methoxybenzyl; 3,4-dimethoxybenzyl; and nitrobenzyl).

Other N-protecting groups include, but are not limited to, chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, arylalkyl groups such as benzyl, triphenylmethyl, benzyloxymethyl, and the like and silyl groups such as trimethylsilyl, and the like. Useful N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "selective CDK6 inhibitor," as used herein, represents a CDK6 inhibitor that upon contacting a CDK6$^{-/-}$ cell (e.g., a CDK6$^{-/-}$ MEF cell) inhibits the cell proliferation with IC50 that is at least five-fold (preferably, 10-fold) greater than the CDK6 inhibitor IC50 for the corresponding cell expressing CDK6 (e.g., a WT-MEF cell).

The term "subject," as used herein, represents a human or non-human animal (e.g., a mammal) that is suffering from cancer (e.g., leukemia, lung cancer, or brain tumor) or metabolic diseases (e.g., obesity), as determined by a qualified professional (e.g., a doctor or a nurse practitioner) with or without known in the art laboratory test(s) of sample(s) from the patient.

The term "treating" as used in reference to a disease or a condition in a patient, is intended to refer to obtaining beneficial or desired results, e.g., clinical results, in a patient by administering a compound of the invention to the patient. Beneficial or desired results may include alleviation or amelioration of one or more symptoms of a disease or condition; diminishment of extent of a disease or condition; stabilization (i.e., not worsening) of a disease or condition; prevention of the spread of a disease or condition; delay or slowing the progress of a disease or condition; palliation of a disease or condition; and remission (whether partial or total). "Palliating" a disease or condition means that the extent and/or undesirable clinical manifestations of the disease or condition are lessened and/or time course of the progression is slowed, as compared to the extent or time course in the absence of the treatment with the compound of the invention.

BRIEF DESCRIPTION OF THE DRAWINGS

FIGS. 9A and 9B are images showing a close view of the iWAT (FIG. 9A) and eWAT (FIG. 9B) and mass of fat pads from mice treated with GD or PBS, as indicated. The mass of various fat pads was normalized to body weight of mice on NCD at the end of experiments. Data shown are mean±S.D. (n=8 for each group), *p<0.05, t-test, GD vs PBS.

FIG. 9C is a graph showing the changes in the samples illustrated in FIGS. 9A and 9B.

FIG. 9D is a graph showing body weight of age-matched female WT mice on NCD over 27-day observation period. GD/PBS commenced by gavage daily for 21 days at 200 mg/kg/day at age of 6-weeks-old. Body weight shown are mean±S.D. (n=8 for each group), *p<0.05, t-test, GD vs PBS.

FIG. 10A is a graph showing suppressed xenograft tumor growth in nude mice treated with GD. A549 cells (3×10⁵/each side) were inoculated ectopically in female Nod/Scid mice. One week after inoculation, tumor bearing mice were treated with GD at 200 mg/kg/day or PBS by oral gavage for 21 days. Data shown are mean±S.D. (n=8 for each group), *p<0.05, t-test, GD vs. PBS.

FIG. 10B is a graph showing body weight of two groups of mice during the observation time. Body weights shown are mean±S.D. (n=4 for each group).

FIG. 10C is an image showing a close view of tumor bearing mice at the end of the experiments (day 27). The top 4 mice were treated with GD and the bottom 4 mice were treated with PBS.

FIG. 10D is an image showing a close view of tumors isolated from two groups of mice treated with GD (on the top panel) or PBS (on the bottom panel) as indicated.

DETAILED DESCRIPTION

Figure 1A:
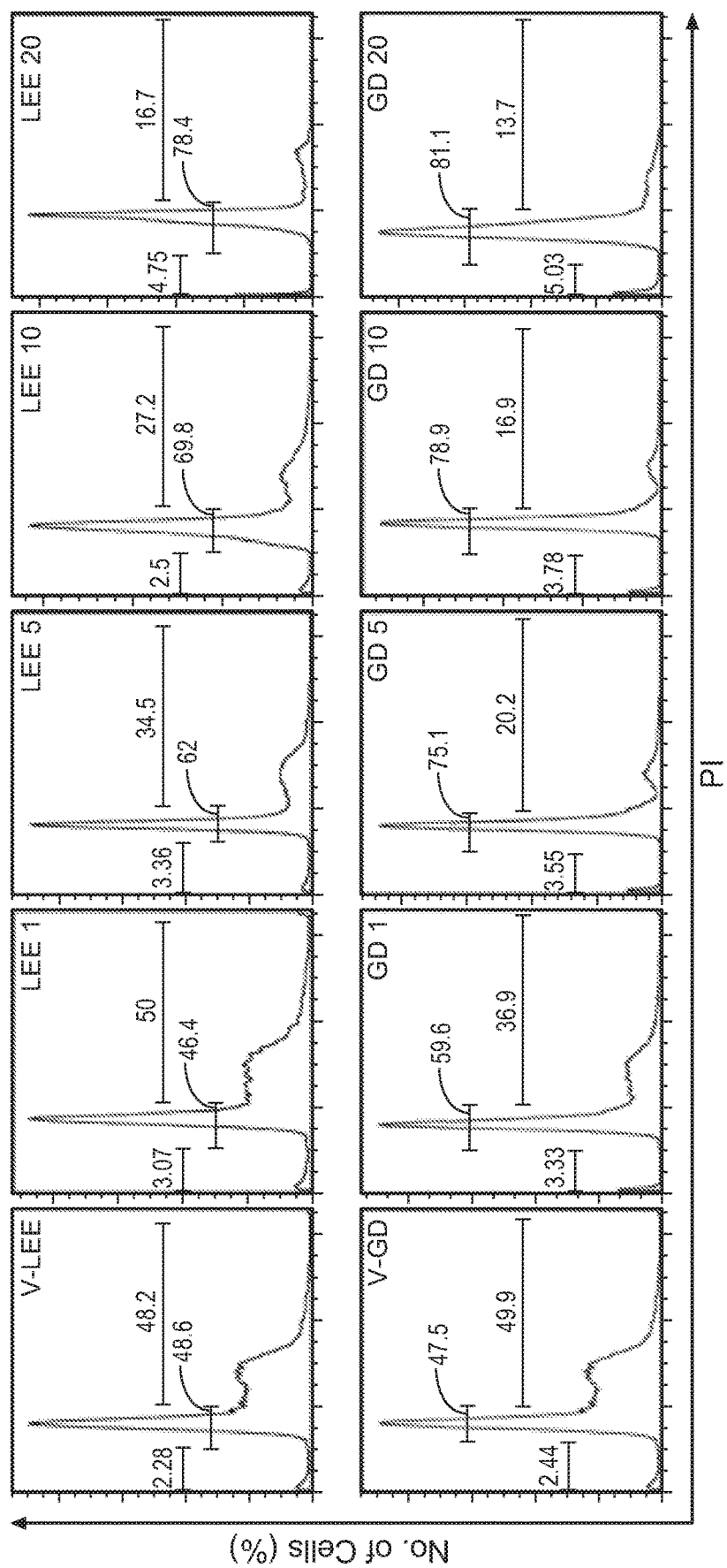
FIG. 1A is a series of charts showing representative cell cycle profiles of human leukemia cell line HPBALL (with Notch1 mutations) treated with a vehicle (V) (for ribociclib (LEE) or compound GD) or LEE or compound GD for 6 days at 1, 5, 10, and 20 µM.
Figure 1B:
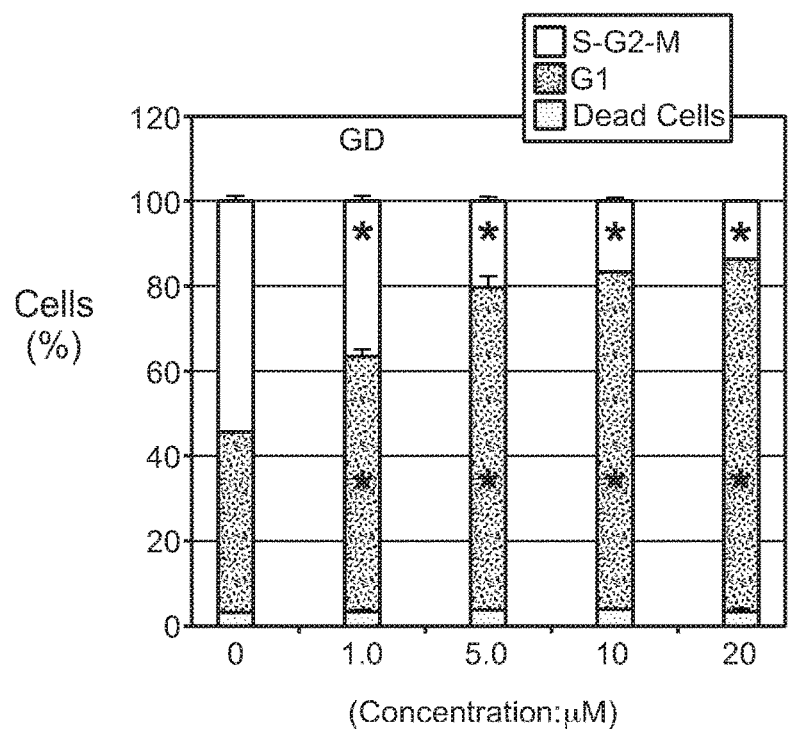
FIG. 1B is a histogram summarizing the cell cycle distribution of the HPBALL cell line treated with compound GD, as described for FIG. 1A. Data shown are mean±S.D. (n=6); *P<0.05 vs its vehicle controls, t-test.
Figure 1C:
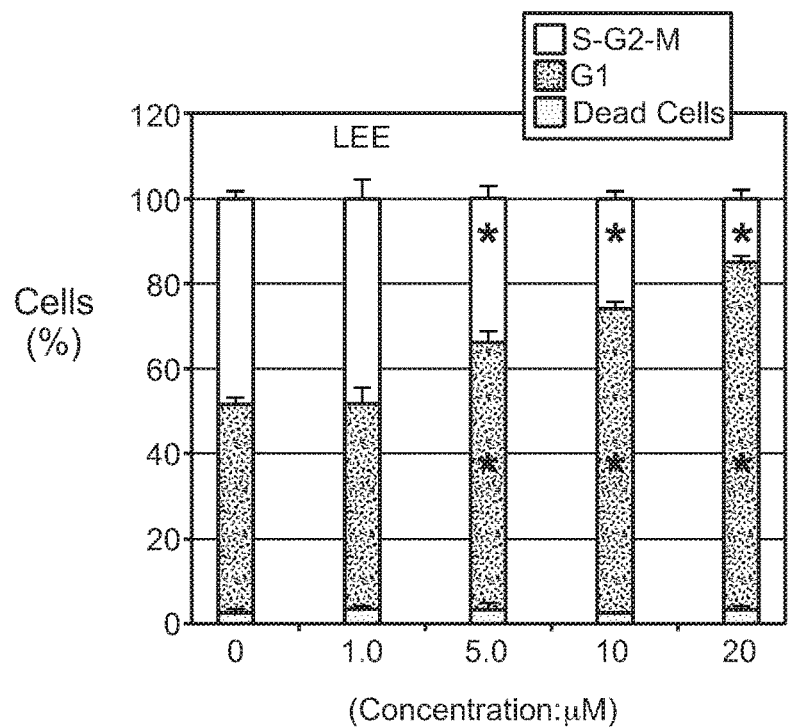
FIG. 1C is a histogram summarizing the cell cycle distribution of the HPBALL cell line treated with ribociclib (LEE), as described for FIG. 1A. Data shown are mean±S.D. (n=6); *P<0.05 vs its vehicle controls, t-test.
Figure 1D:
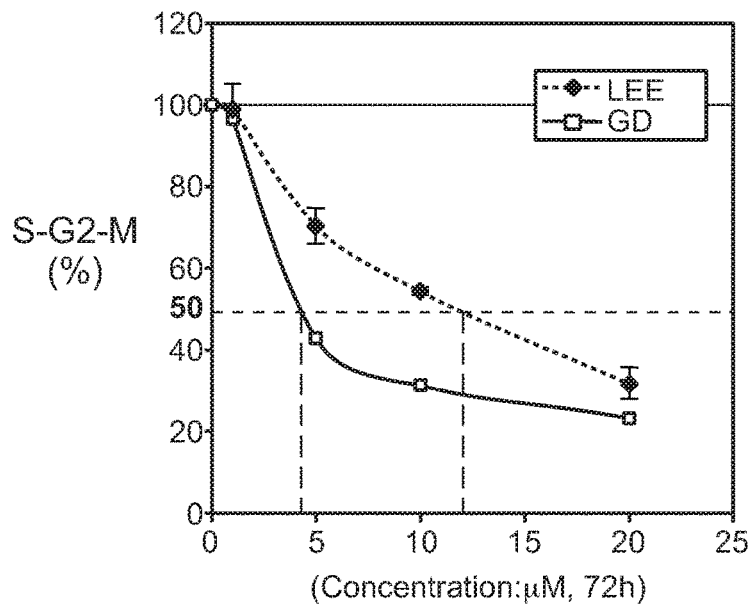
FIG. 1D is a chart the percentage of S-G2-M cells in FIGS. 1B and 1C. IC50 is the concentration of an inhibitor where the response (here is the inhibition of proliferation) is reduced by half. Observed IC50 for LEE is ca. 12 µM, and observed IC50 for GD is ca. 4 µM.
Figure 1E:
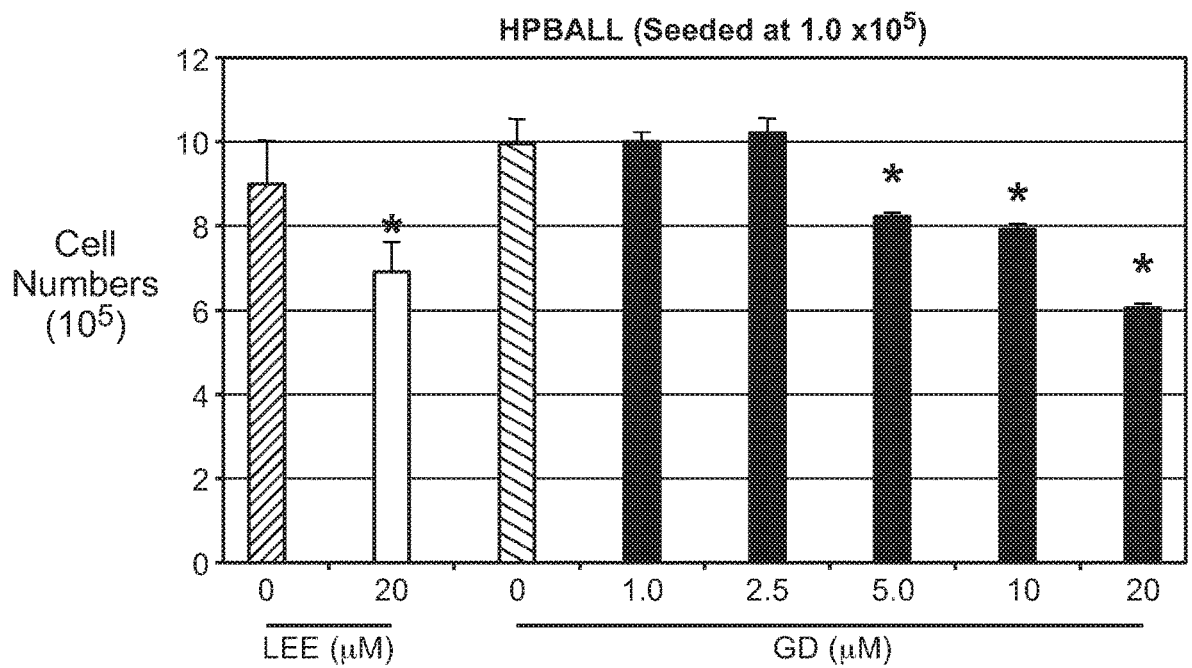
FIG. 1E is a bar graph summarizing the cell numbers of HPBALL cells treated with either GD with different doses or LEE (20 µM) for 6 days. Data shown are mean±S.D. (n=6); *P<0.05 vs vehicles (0) control, t-test.
Figure 2A:
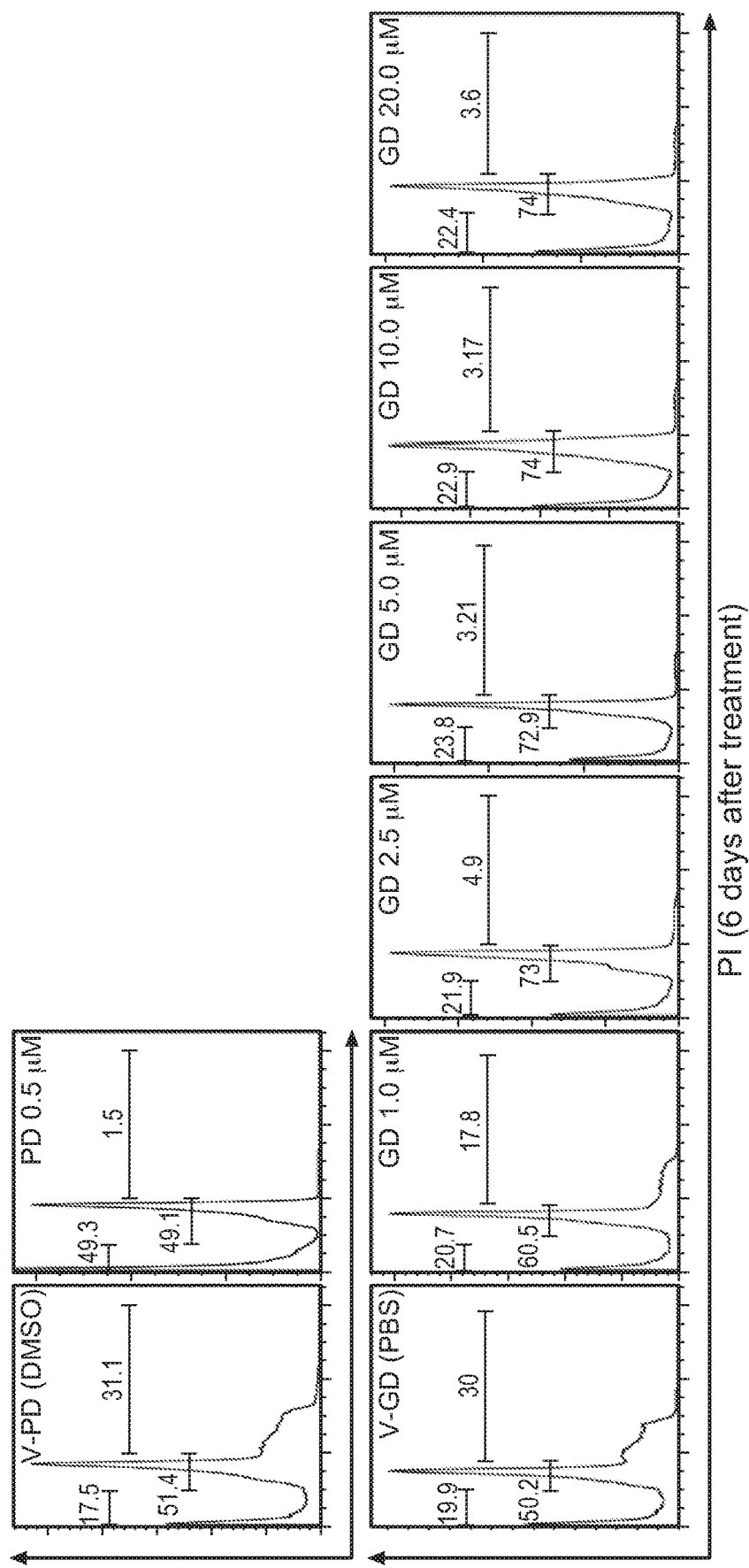
FIG. 2A is a series of charts showing representative cell cycle profiles of human leukemia cell line T-ALL1 (with WT Notch1) treated with a vehicle (V) (for palbociclib (PD) or compound GD), PD (0.5 µM), or compound GD at 1, 2.5, 5, 10, and 20 µM for 6 days.
Figure 2B:
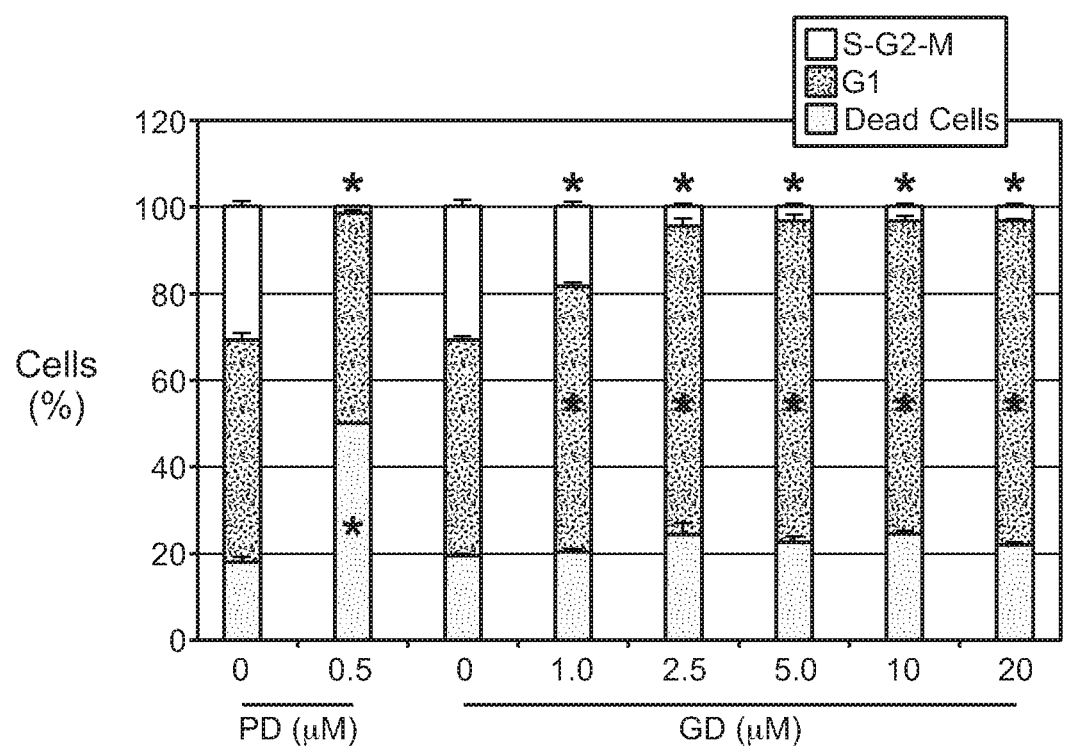
FIG. 2B is a histogram summarizing the cell cycle distribution of the T-ALL1 cell line in FIG. 2A. Data shown are mean±S.D. (n=6); *P<0.05 vs its vehicle controls, t-test.
Figure 2C:
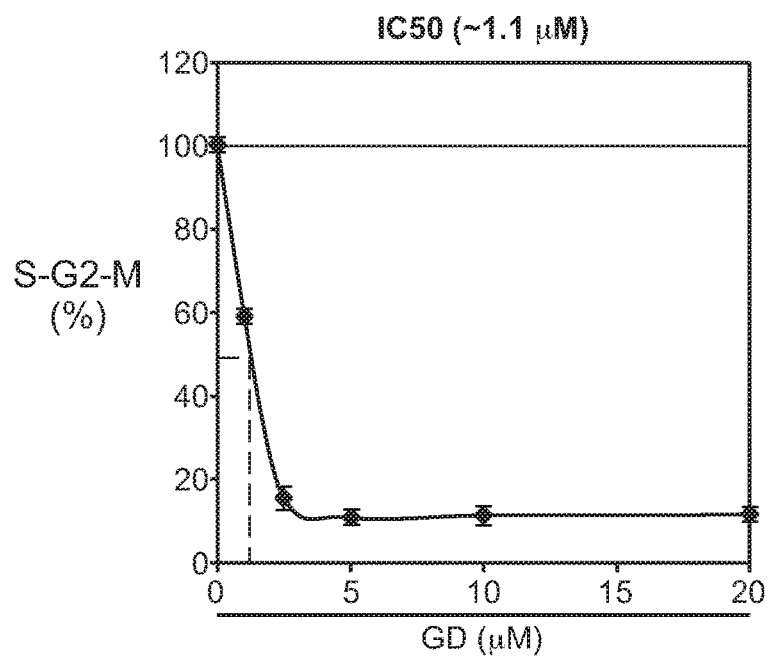
FIG. 2C is a chart showing the percentage of S-G2-M cells in samples in FIGS. 2A and 2B. IC50 for GD is ca. 1.1 µM.
Figure 2D:
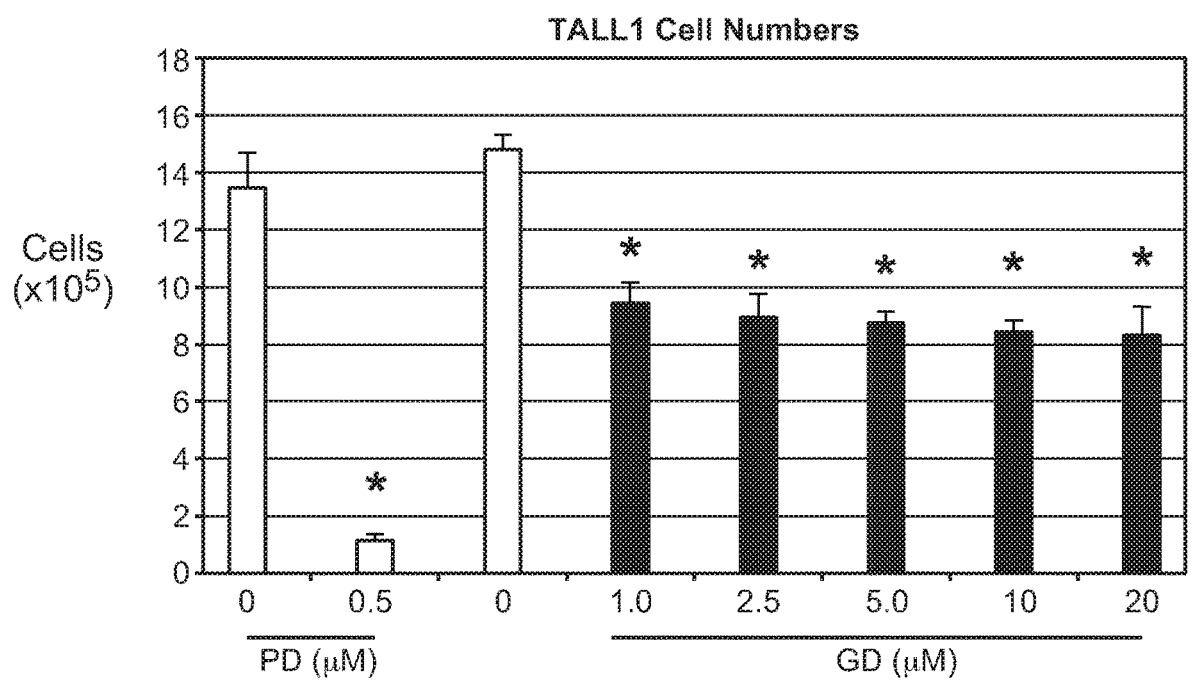
FIG. 2D is a bar graphs summarizing the cell numbers of T-ALL1 cells treated with either compound GD at different doses or with palbociclib (PD (0.5 µM) for 6 days. Data shown are mean±S.D. (n=6); *P<0.05 vs vehicles (0) control, t-test.

The invention provides compounds, pharmaceutical compositions containing the compounds, and methods of their use. The compounds disclosed herein include compounds of formula (I):

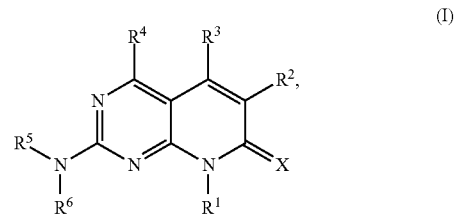

or a pharmaceutically acceptable salt thereof, where
X is O or S;
R¹ is hydrogen, an optionally substituted $C_{1-6}$ alkyl, or an optionally substituted $C_{3-8}$ cycloalkyl;
each of R², R³, and R⁴ is independently hydrogen, halo, or an optionally substituted $C_{1-6}$ alkyl;
R⁵ is a substituted $C_3$ heteroaryl; and
R⁶ is hydrogen or an optionally substituted $C_{1-6}$ alkyl.

In some embodiments, R⁵ is a substituted thiazolyl or substituted oxazolyl (e.g., substituted with an optionally substituted $C_{1-9}$ heterocyclyl $C_{1-6}$ alkyl). In further embodiments, R⁵ is a group of formula:

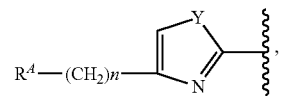

where
n is an integer from 0 to 6;
Y is S or O; and
$R^A$ is an optionally substituted $C_{1-9}$ heterocyclyl.
In some embodiments, Y is S.
A non-limiting example of the compound of formula (I) is:

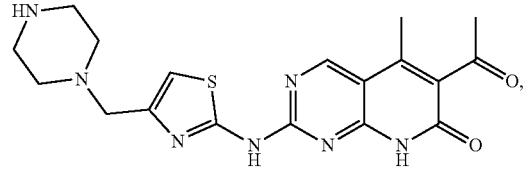 [SMILES: CC(=O)c1c(C)c2cnc(Nc3nc(CN4CCNCC4)cs3)nc2[nH]c1=O]

or a pharmaceutically acceptable salt thereof.

Without wishing to be bound by theory, it is believed that the compounds described herein may act as an inhibitor of cyclin-dependent kinase 6 (CDK6) to provide the therapeutic benefits described herein.

Advantageously, the compounds described herein may be selective CDK6 inhibitors. Without wishing to be bound by theory, it is believed that inhibition of cyclin-dependent kinase 4 (CDK4) activity can result in insulin-deficient diabetes due to a severe reduction in the β-cell growth. The compounds disclosed herein (e.g., selective CDK6 inhibitors) may exhibit reduced toxicity and, therefore, may produce fewer and/or milder adverse events (e.g., adverse events associated with insulin-deficient diabetes associated with the CDK4 inhibition), e.g., relative to CDK6 inhibitors that also inhibit CDK4.

Compound Preparation

A compound of formula (I) may be prepared by reacting a compound of formula (IA) with a compound of formula (IB) under conditions permitting for a substitution reaction to occur between these compounds. The compound of formula (IA) is:

of the N-protecting group. N-protecting groups and reaction conditions for their removal are known in the art. Similarly, any other protecting groups (e.g., O-protecting groups and N-protecting groups) present in the substitution reaction product may be removed using reaction conditions known in the art.

An exemplary compound of formula (IA) may be prepared, for example, as shown in Scheme 1.

Scheme 1

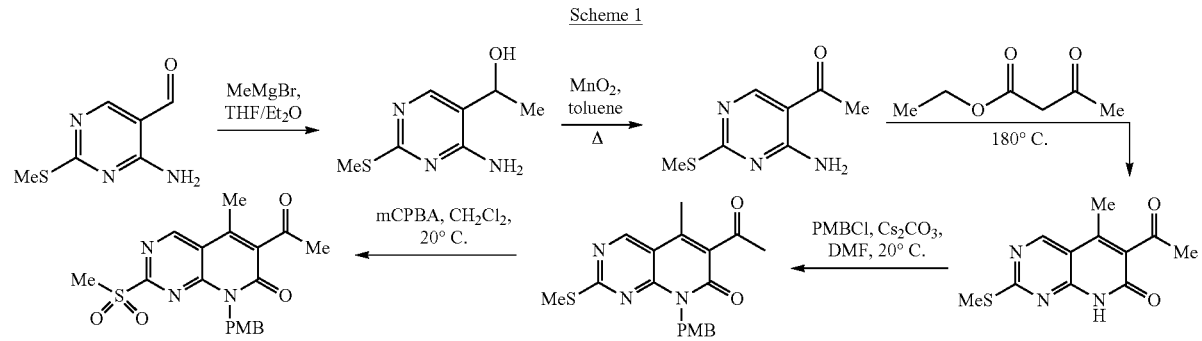

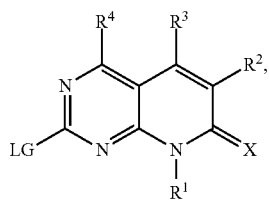

(IA)

or a salt thereof, where

X is O or S;

LG is a leaving group (e.g., alkylsulfonyl);

$R^1$ is an N-protecting group, optionally substituted $C_{1-6}$ alkyl, or optionally substituted $C_{3-8}$ cycloalkyl; and each of $R^2$, $R^3$, and $R^4$ is independently hydrogen, halo, or an optionally substituted $C_{1-6}$ alkyl.

The compound of formula (IB) is:

$R^5$—NH—$R^6$, (IB)

or a salt thereof, where $R^5$ is a substituted, optionally protected $C_3$ heteroaryl; and $R^6$ is hydrogen or an optionally substituted $C_{1-6}$ alkyl.

The substitution reaction conditions are known in the art. In a non-limiting example, compound (IA) and compound (IB) may be reacted in an aprotic solvent (e.g., toluene) at elevated temperatures (e.g., up to the boiling point of the aprotic solvent).

When $R^1$ in the compound of formula (IA) is an N-protecting group, preparation of a compound of formula (I) may further include subjecting the product of the substitution reaction to the reaction conditions suitable for the removal Other compounds of formula (IA) may also be prepared using the synthesis strategy shown in Scheme 1.

An exemplary compound of formula (IB) may be prepared, for example, as shown in Scheme 2.

Scheme 2

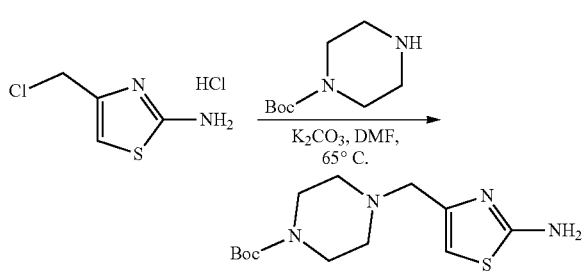

Other compounds of formula (IB) may also be prepared using the synthesis strategy shown in Scheme 2.

Therapeutic Methods

CDK6 inhibitors can be used in the treatment of cancer (e.g., T-ALLs). Accordingly, compounds disclosed herein, which have CDK6 inhibitory activity, can be used in methods of treating subjects having cancer (e.g., leukemia, lung cancer, brain tumor, cervical cancer, or pancreatic cancer). In some embodiments, the leukemia is acute lymphoblastic leukemia (e.g., T-cell acute lymphoblastic leukemia).

The compounds disclosed herein can further be used in the treatment and prevention of metabolic diseases. In particular, in mammals including humans, fat is stored in white adipose tissue (WAT) in the form of triglycerides, whereas brown fat cells (BAT) have the ability to burn energy through adaptive thermogenesis. Inducible-brown adipocytes (beige or brite cells) are found sporadically in WAT and are associated with protection against obesity and metabolic diseases. Furthermore, CDK6 is an important regulator of white fat browning (WO 2017/161253). As a CDK6 inhibitory compound disclosed herein induces beige cell formation, but inhibits white adipocyte formation (see FIGS. 8A-8C), the compounds of the invention can advantageously be used in the treatment and prevention of metabolic diseases and obesity. Accordingly, compounds disclosed herein can be used in methods of treating subjects having or at risk of developing a metabolic disease (e.g., obesity, type II diabetes, metabolic syndrome, elevated blood pressure, a cardiovascular disease, elevated fasting plasma glucose, or a high level of serum triglycerides).

The methods disclosed herein typically include administering to a subject in need thereof an effect amount of a compound disclosed herein (e.g., in a pharmaceutical composition).

The compounds used in the methods described herein can be administered, for example, by oral, parenteral, buccal, sublingual, nasal, rectal, patch, pump, or transdermal administration, and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

Compounds disclosed herein can further be used to induce cell death in cancer cells by contacting the cancer cells with a compound disclosed herein. Non-limiting examples of cancer cells in which cell death can be induced include leukemic cells, cervical cancer cells, lung cancer cells, brain tumor cells, and pancreatic cancer cells.

Pharmaceutical Compositions

The compounds used in the methods described herein are preferably formulated into pharmaceutical compositions for administration to human subjects in a biologically compatible form suitable for administration in vivo. Pharmaceutical compositions typically include a compound as described herein and a pharmaceutically acceptable excipient.

The compounds described herein can also be used in the form of the free base, in the form of salts (e.g., HCl salt), zwitterions, solvates, or as prodrugs, or pharmaceutical compositions thereof. All forms are within the scope of the invention. The compounds, salts, zwitterions, solvates, prodrugs, or pharmaceutical compositions thereof, may be administered to a patient in a variety of forms depending on the selected route of administration, as will be understood by those skilled in the art. The compounds used in the methods described herein may be administered, for example, by oral, parenteral, buccal, sublingual, nasal, rectal, patch, pump, or transdermal administration, and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

For human use, a compound of the invention can be administered alone or in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of a compound of the invention into preparations which can be used pharmaceutically.

This invention also includes pharmaceutical compositions which can contain one or more pharmaceutically acceptable carriers. In making the pharmaceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, e.g., preservatives.

The excipient or carrier is selected on the basis of the mode and route of administration. Suitable pharmaceutical carriers, as well as pharmaceutical necessities for use in pharmaceutical formulations, are described in *Remington: The Science and Practice of Pharmacy*, 21$^{st}$ Ed., Gennaro, Ed., Lippincott Williams & Wilkins (2005), a well-known reference text in this field, and in the USP/NF (United States Pharmacopeia and the National Formulary). Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents, e.g., talc, magnesium stearate, and mineral oil; wetting agents; emulsifying and suspending agents; preserving agents, e.g., methyl- and propylhydroxy-benzoates; sweetening agents; and flavoring agents. Other exemplary excipients are described in *Handbook of Pharmaceutical Excipients*, 6$^{th}$ Edition, Rowe et al., Eds., Pharmaceutical Press (2009).

These pharmaceutical compositions can be manufactured in a conventional manner, e.g., by conventional mixing, dissolving, granulating, dragee-making, levigating, emulsifying, encapsulating, entrapping, or lyophilizing processes. Methods well known in the art for making formulations are found, for example, in *Remington: The Science and Practice of Pharmacy*, 21$^{st}$ Ed., Gennaro, Ed., Lippincott Williams & Wilkins (2005), and Encyclopedia of Pharmaceutical Technology, eds. J. Swarbrick and J. C. Boylan, 1988-1999, Marcel Dekker, New York. Proper formulation is dependent upon the route of administration chosen. The formulation and preparation of such compositions is well-known to those skilled in the art of pharmaceutical formulation. In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

Dosages

The dosage of the compound used in the methods described herein, or pharmaceutically acceptable salts or prodrugs thereof, or pharmaceutical compositions thereof, can vary depending on many factors, e.g., the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds used in the methods described herein may be administered initially in a suitable dosage that may be adjusted as required, depending on the clinical response. In general, a suitable daily dose of a compound of the invention will be that amount of the compound that is the lowest dose effective to produce a therapeutic effect. Such an effective dose will generally depend upon the factors described above.

A compound of the invention may be administered to the patient in a single dose or in multiple doses. When multiple doses are administered, the doses may be separated from one another by, for example, 1-24 hours, 1-7 days, 1-4 weeks, or 1-12 months. The compound may be administered according to a schedule or the compound may be administered without a predetermined schedule. An active compound may be administered, for example, 1, 2, 3, 4, 5, 6, 7, 8, 9, 10, 11, or 12 times per day, every $2^{nd}$, $3^{rd}$, $4^{th}$, $5^{th}$ or $6^{th}$ day, 1, 2, 3, 4, 5, 6, or 7 times per week, 1, 2, 3, 4, 5, or 6 times per month, or 1, 2, 3, 4, 5, 6, 7, 8, 9, 10, 11, or 12 times per year. It is to be understood that, for any particular subject, specific dosage regimes should be adjusted over time according to the individual need and the professional judgment of the person administering or supervising the administration of the compositions.

While the attending physician ultimately will decide the appropriate amount and dosage regimen, an effective amount of a compound of the invention may be, for example, a total daily dosage of, e.g., between 0.05 mg and 3000 mg of any of the compounds described herein. Alternatively, the dosage amount can be calculated using the body weight of the patient. Such dose ranges may include, for example, between 10-1000 mg (e.g., 50-800 mg). In some embodiments, 50, 100, 150, 200, 250, 300, 350, 400, 450, 500, 550, 600, 650, 700, 750, 800, 850, 900, 950, or 1000 mg of the compound is administered.

In the methods of the invention, the time period during which multiple doses of a compound of the invention are administered to a patient can vary. For example, in some embodiments doses of the compounds of the invention are administered to a patient over a time period that is 1-7 days; 1-12 weeks; or 1-3 months. In other embodiments, the compounds are administered to the patient over a time period that is, for example, 4-11 months or 1-30 years. In other embodiments, the compounds are administered to a patient at the onset of symptoms. In any of these embodiments, the amount of compound that is administered may vary during the time period of administration. When a compound is administered daily, administration may occur, for example, 1, 2, 3, 4, 5, 6, 7, 8, 9, 10, 11, or 12 times per day.

Formulations

A compound identified as capable of treating any of the conditions described herein, using any of the methods described herein, may be administered to patients or animals with a pharmaceutically-acceptable diluent, carrier, or excipient, in unit dosage form. The chemical compounds for use in such therapies may be produced and isolated by any standard technique known to those in the field of medicinal chemistry. Conventional pharmaceutical practice may be employed to provide suitable formulations or compositions to administer the identified compound to patients suffering from a bacterial infection. Administration may begin before the patient is symptomatic.

Exemplary routes of administration of the compounds (e.g., a compound of the invention), or pharmaceutical compositions thereof, used in the present invention include oral, sublingual, buccal, transdermal, intradermal, intramuscular, parenteral, intravenous, intra-arterial, intracranial, subcutaneous, intraorbital, intraventricular, intraspinal, intraperitoneal, intranasal, inhalation, and topical administration. The compounds desirably are administered with a pharmaceutically acceptable carrier. Pharmaceutical formulations of the compounds described herein formulated for treatment of the disorders described herein are also part of the present invention.

Formulations for Oral Administration

The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration versus time profile. In one example, controlled release is obtained by appropriate selection of various formulation parameters and ingredients, including, e.g., various types of controlled release compositions and coatings. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils, e.g., cottonseed oil, sesame oil, coconut oil, or peanut oil, as well as elixirs and similar pharmaceutical vehicles.

Formulations for Buccal Administration

Dosages for buccal or sublingual administration typically are 0.1 to 500 mg per single dose as required. In practice, the physician determines the actual dosing regimen which is most suitable for an individual patient, and the dosage varies with the age, weight, and response of the particular patient. The above dosages are exemplary of the average case, but individual instances exist wherein higher or lower dosages are merited, and such are within the scope of this invention.

For buccal administration, the compositions may take the form of tablets, lozenges, etc. formulated in a conventional manner. Liquid drug formulations suitable for use with nebulizers and liquid spray devices and electrohydrodynamic (EHD) aerosol devices will typically include a compound of the invention with a pharmaceutically acceptable carrier. Preferably, the pharmaceutically acceptable carrier is a liquid, e.g., alcohol, water, polyethylene glycol, or a perfluorocarbon. Optionally, another material may be added to alter the aerosol properties of the solution or suspension of compounds of the invention. Desirably, this material is liquid, e.g., an alcohol, glycol, polyglycol, or a fatty acid. Other methods of formulating liquid drug solutions or suspension suitable for use in aerosol devices are known to those of skill in the art (see, e.g., Biesalski, U.S. Pat. No. 5,112,598 and Biesalski, U.S. Pat. No. 5,556,611, each of which is herein incorporated by reference).

Formulations for Nasal or Inhalation Administration

The compounds may also be formulated for nasal administration. Compositions for nasal administration also may conveniently be formulated as aerosols, drops, gels, and powders. The formulations may be provided in a single or multidose form. In the case of a dropper or pipette, dosing may be achieved by the patient administering an appropriate, predetermined volume of the solution or suspension. In the case of a spray, this may be achieved, for example, by means of a metering atomizing spray pump.

The compounds may further be formulated for aerosol administration, particularly to the respiratory tract by inhalation and including intranasal administration. The compound will generally have a small particle size for example on the order of five (5) microns or less. Such a particle size may be obtained by means known in the art, for example by micronization. The active ingredient is provided in a pressurized pack with a suitable propellant, e.g., a chlorofluorocarbon (CFC), for example, dichlorodifluoromethane, trichlorofluoromethane, or dichlorotetrafluoroethane, or carbon dioxide, or other suitable gas. The aerosol may conveniently also contain a surfactant, e.g., lecithin. The dose of drug may be controlled by a metered valve. Alternatively, the active ingredients may be provided in a form of a dry powder, e.g., a powder mix of the compound in a suitable powder base, e.g., lactose, starch, and starch derivatives, e.g., hydroxypropylmethyl cellulose, and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, e.g., a single dose nasal inhaler or an aerosol dispenser fitted with a metering valve which is intended for disposal after use. Where the dosage form comprises an aerosol dispenser, it will contain a propellant, which can be a compressed gas, e.g., compressed air or an organic propellant, e.g., fluorochlorohydrocarbon. The aerosol dosage forms can also take the form of a pump-atomizer.

Formulations for Parenteral Administration

The compounds described herein for use in the methods of the invention can be administered in a pharmaceutically acceptable parenteral (e.g., intravenous or intramuscular) formulation as described herein. The pharmaceutical formulation may also be administered parenterally (intravenous, intramuscular, subcutaneous or the like) in dosage forms or formulations containing conventional, non-toxic pharmaceutically acceptable carriers and adjuvants. In particular, formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. For example, to prepare such a composition, the compounds of the invention may be dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl, or n-propyl p-hydroxybenzoate. Additional information regarding parenteral formulations can be found, for example, in the United States Pharmacopeia-National Formulary (USP-NF), herein incorporated by reference.

The parenteral formulation can be any of the five general types of preparations identified by the USP-NF as suitable for parenteral administration:

(1) "Drug Injection:" a liquid preparation that is a drug substance (e.g., a compound of the invention), or a solution thereof;

(2) "Drug for Injection:" the drug substance (e.g., a compound of the invention) as a dry solid that will be combined with the appropriate sterile vehicle for parenteral administration as a drug injection;
(3) "Drug Injectable Emulsion:" a liquid preparation of the drug substance (e.g., a compound of the invention) that is dissolved or dispersed in a suitable emulsion medium;
(4) "Drug Injectable Suspension:" a liquid preparation of the drug substance (e.g., a compound of the invention) suspended in a suitable liquid medium; and
(5) "Drug for Injectable Suspension:" the drug substance (e.g., a compound of the invention) as a dry solid that will be combined with the appropriate sterile vehicle for parenteral administration as a drug injectable suspension.

Exemplary formulations for parenteral administration include solutions of the compound prepared in water suitably mixed with a surfactant, e.g., hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in *Remington: The Science and Practice of Pharmacy*, 21$^{st}$ Ed., Gennaro, Ed., Lippincott Williams & Wilkins (2005) and in the United States Pharmacopeia: the National Formulary (USP 36 NF31), published in 2013.

Formulations for parenteral administration may, for example, contain excipients, sterile water, or saline, polyalkylene glycols, e.g., polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The parenteral formulation can be formulated for prompt release or for sustained/extended release of the compound. Exemplary formulations for parenteral release of the compound include: aqueous solutions, powders for reconstitution, cosolvent solutions, oil/water emulsions, suspensions, oil-based solutions, liposomes, microspheres, and polymeric gels.

The following examples are meant to illustrate the invention. They are not meant to limit the invention in any way.

EXAMPLES

Example 1

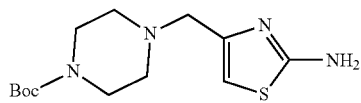 [SMILES: CC(C)(C)OC(=O)N1CCN(Cc2csc(N)n2)CC1]

Tert-butyl 4-((2-aminothiazol-4-yl)methyl)piperazine-1-carboxylate. To a solution of 4-(chloromethyl)thiazol-2-amine (25.0 g, 0.13 mol) in N,N-dimethylformamide (150 mL) were added tert-butyl piperazine-1-carboxylate (25.1 g, 0.13 mol) and $K_2CO_3$ (46.6 g, 0.34 mol). The resulting mixture was stirred at 65° C. for 16 h. The mixture was then diluted with water (200 mL), and the product was extracted with ethyl acetate (150 mL×3). The combined organic layers were dried, concentrated, and purified by silica gel chromatography (dichloromethane/methanol=20/1 to 10/1) to give tert-butyl 4-((2-aminothiazol-4-yl)methyl)piperazine-1-carboxylate (25.0 g, 62% yield) as white solid. $^1$H NMR (DMSO-d6, 400 MHz) δ: 6.85 (s, 2H), 6.30 (s, 1H), 3.25-3.4 (m, 6H), 2.33-2.35 (br. s., 4H), 1.38 (s, 9H). LC-MS: m/z 299.2 (M+H)$^+$.

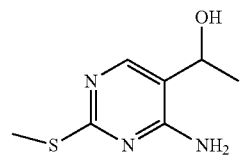

1-(4-amino-2-(methylthio)pyrimidin-5-yl)ethanol. To a suspension of 4-amino-2-(methylthio)pyrimidine-5-carbaldehyde (80 g, 0.47 mol) in tetrahydrofuran (300 mL) was slowly added methylmagnesium bromide (470 mL, 3M), and the resulting mixture was stirred at 0° C. for 2 h, at which time the reaction was quenched with sat. aq. $NH_4Cl$. The product was then extracted with ethyl acetate (200 mL×3). The combined organic layers were dried, concentrated, and purified by silica gel chromatography (dichloromethane/methanol=30/1) to get 1-(4-amino-2-(methylthio)pyrimidin-5-yl)ethanol (60 g, 69% yield) as a light yellow solid. $^1$H NMR (DMSO-d6, 400 MHz) δ: 7.82 (s, 1H), 5.64 (br. s., 2H), 4.82 (q, J=6.7 Hz, 1H), 2.49 (s, 3H), 1.54 (d, J=6.4 Hz, 3H) LC-MS: m/z 186.5 (M+H)$^+$.

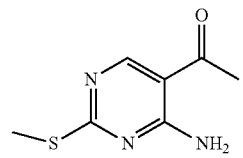

1-(4-amino-2-(methylthio)pyrimidin-5-yl)ethanone. To a suspension of 1-(4-amino-2-(methylthio)pyrimidin-5-yl)ethanol (60 g, 0.32 mol) in toluene (600 mL) was added manganese(IV) oxide (70 g, 0.81 mol). The resulting mixture was stirred at 120° C. for 4 h, at which time the mixture was diluted with 200 mL of 1:1 tetrahydrofuran/methanol and filtered. The filtrate was concentrated to give the desired product (50.0 g, 83% yield) as white solid. $^1$H NMR (DMSO-d6, 400 MHz) δ: 8.76 (s, 1H), 8.43 (br. s, 1H), 8.07 (br. s., 1H), 2.50 (s, 3H), 2.48 (s, 3H). LC-MS: m/z 184.1 (M+H)$^+$

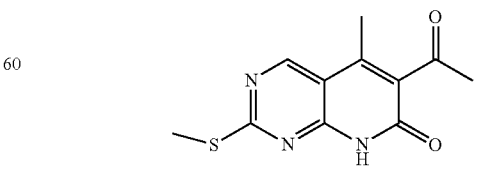

6-acetyl-5-methyl-2-(methylthio)pyrido[2,3-d]pyrimidin-7(8H)-one. The suspension of 1-(4-amino-2-(methylthio)

pyrimidin-5-yl)ethanone (10.0 g, 54.6 mmol) in ethyl 3-oxobutanoate (30 mL) was stirred at 180° C. for 4 h. Then the mixture was cooled to room temperature, and ethyl acetate (50 mL) was added. The resulting mixture was then filtered, washed with ethyl acetate (10 mL), and dried to give the desired product (10.0 g, 73% yield) as white solid. $^1$H NMR (DMSO-d6, 400 MHz) δ: 12.62 (s, 1H), 9.02 (s, 1H), 2.58 (s, 3H), 2.45 (s, 3H), 2.35 (s, 3H). LC-MS: m/z 250.3 (M+H)$^+$

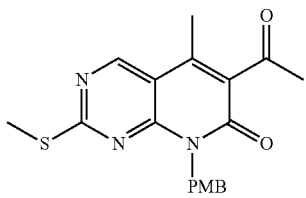

6-acetyl-8-(4-methoxybenzyl)-5-methyl-2-(methylthio) pyrido[2,3-d]pyrimidin-7(8H)-one. To a solution of 6-acetyl-5-methyl-2-(methylthio)pyrido[2,3-d]pyrimidin-7 (8H)-one (10 g, 40.1 mmol) in N,N-dimethylformamide (200 mL) was added Cs$_2$CO$_3$ (26.2 g, 80.2 mmol) and 1-(bromomethyl)-4-methoxybenzene (6.2 g, 40.1 mmol), and the resulting mixture was stirred at room temperature for 1 h. The mixture was filtered, and the filtrate was concentrated, followed by purification by reverse phase column chromatography (water/methanol=gradient from 10% to 100%) to give the desired product (5 g, 33%) as a yellow solid. $^1$H NMR (DMSO-d6, 400 MHz) δ: 9.07 (s, 1H), 7.27 (d, J=8.8 Hz, 2H), 6.86 (d, J=9.2 Hz, 2H), 5.44 (s, 2H), 3.70 (s, 3H), 2.58 (s, 3H), 2.46 (s, 3H), 2.37 (s, 3H). LC-MS: m/z 370.2 (M+H)$^+$

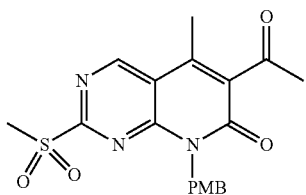

6-acetyl-8-(4-methoxybenzyl)-5-methyl-2-(methylsulfonyl)pyrido[2,3-d]pyrimidin-7(8H)-one. To a solution of 6-acetyl-8-(4-methoxybenzyl)-5-methyl-2-(methylthio) pyrido[2,3-d]pyrimidin-7(8H)-one (5.0 g, 13.5 mmol) in dichloromethane (100 mL) was added 3-chloroperoxybenzoic acid (5.8 g, 33.8 mmol). The resultant mixture was stirred at room temperature for 0.5 h. Then the mixture was washed with NaHSO$_3$ solution. The aqueous solution was extracted with dichloromethane (10 mL×3). The combined organic layers were dried and concentrated to give the crude solid, which was washed with diethyl ether and dried to give the desired product (4.0 g, 92%) as a white solid. LC-MS: m/z 402.1 (M+H)$^+$

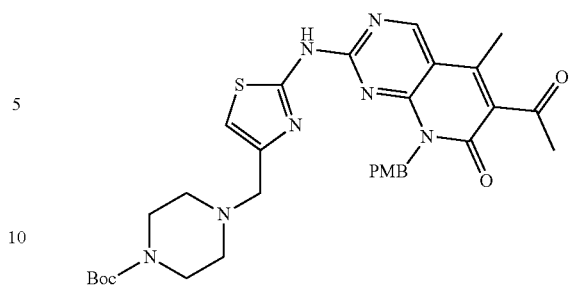

Tert-butyl-4-((2-((6-acetyl-8-(4-methoxybenzyl)-5-methyl-7-oxo-7,8-dihydropyrido[2,3-d]pyrimidin-2-yl) amino)thiazol-4-yl)methyl)piperazine-1-carboxylate. The mixture of 6-acetyl-8-(4-methoxybenzyl)-5-methyl-2-(methylsulfonyl)pyrido[2,3-d]pyrimidin-7(8H)-one (5.0 g, 12.4 mmol) and tert-butyl 4-((2-aminothiazol-4-yl)methyl) piperazine-1-carboxylate (9.2 g, 31.1 mmol) in toluene (50 mL) was stirred at 120° C. overnight. The reaction solution was concentrated to give the crude solid product, which was washed with methanol (20 mL) and filtered to give the desired product (1.5 g, 19%) as a white solid. $^1$H NMR (CDCl$_3$, 400 MHz) δ: 9.11 (br. s., 1H), 7.43 (d, 2H), 6.79 (d, 3H), 5.69 (s., 2H), 3.75 (br. s., 3H), 3.63 (br. s., 2H), 3.49 (br. s., 4H), 2.56 (br. s., 3H), 2.51 (s, 4H), 2.46 (s, 4H), 1.45 (br. s., 9H). LC-MS: m/z 620.3 (M+H)$^+$

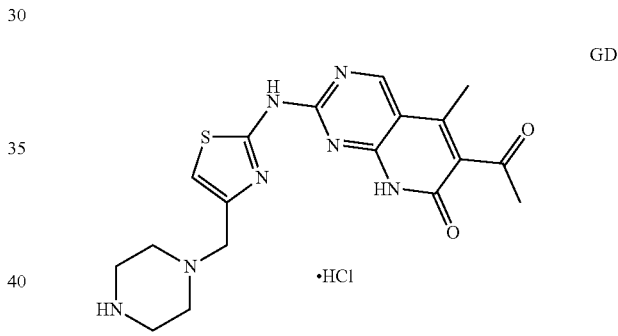

GD

HCl salt of 6-acetyl-5-methyl-2-((4-(piperazin-1-ylmethyl)thiazol-2-yl)amino)pyrido[2,3-d]pyrimidin-7(8H)-one. To a solution of tert-butyl-4-((2-((6-acetyl-8-(4-methoxybenzyl)-5-methyl-7-oxo-7,8-dihydropyrido[2,3-d] pyrimidin-2-yl)amino)thiazol-4-yl)methyl)piperazine-1-carboxylate (13.0 g, 21.0 mmol) in trifluoroacetic acid (150 mL) was added trifluoromethanesulfonic acid (150 mL). The mixture was stirred at room temperature for 3 h. Then the mixture was added dropwise to the ice cooled aq. NaHCO$_3$ solution and pH was maintained at pH>8. The resulting precipitates were collected by filtration and washed with methanol to give the solid. The solid was dissolved in dichloromethane, and HCl/dioxane (2M) was added. The resulting mixture was stirred for 16 h, at which time this mixture was filtered to give the crude solid product which was dissolved in water and purified by preparatory HPLC (solvent A: water; solvent B: acetonitrile; conditions: at 0-25 min gradient from 10% (v/v) B to 95% (v/v) B, at 25-30 min 95% (v/v) B; collected the fraction at 7.04-7.8 min. Column: C18). The desired product was obtained (5.2 g, 56.8%) as yellow solid. $^1$H NMR (DMSO-d6, 400 MHz) δ: 12.62 (br. s., 1H), 12.12 (br. s., 1H), 9.90 (br. s., 2H), 9.08 (s, 1H), 7.56 (s, 1H), 4.39 (s, 2H), 3.45 (br. s., 8H), 2.45 (s, 3H), 2.36 (s, 3H). LC-MS: m/z 399.9 (M+H)$^+$. Compound GD was then tested for compliance with quality standards, and the test results are provided in Table 1.

TABLE 1

| Test Items | Specification | Results | Test Method |
|---|---|---|---|
| Appearance | Yellow solid | Conforms | Visual |
| Purity | >95.0% | 97.3% | HPLC (min) |
| Identification | Spectrum is consistent with structure | Conforms | By NMR (DMSO-$d_6$) |
| | Spectrum is consistent with structure | Conforms | By LCMS |
| Storage | Stored under nitrogen, protected from light, at a temperature of −20° C. | | |
| Shelf life | N/A | | |
| Packaging | According to the client's requirement | | |

Example 2

Figure 3A:
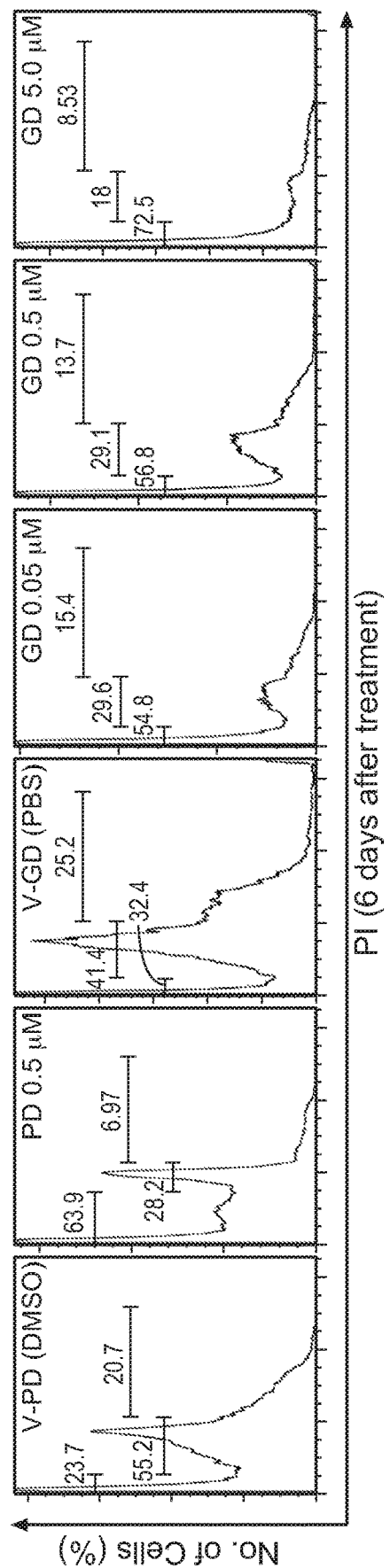
FIG. 3A Representative cell cycle profiles of human leukemia cell line PEER (with WT Notch) treated with a vehicle (V) (for palbociclib (PD) or compound GD), PD (0.5 µM), or compound GD at 0.05, 0.5, and 5 µM for 6 days.
Figure 3B:
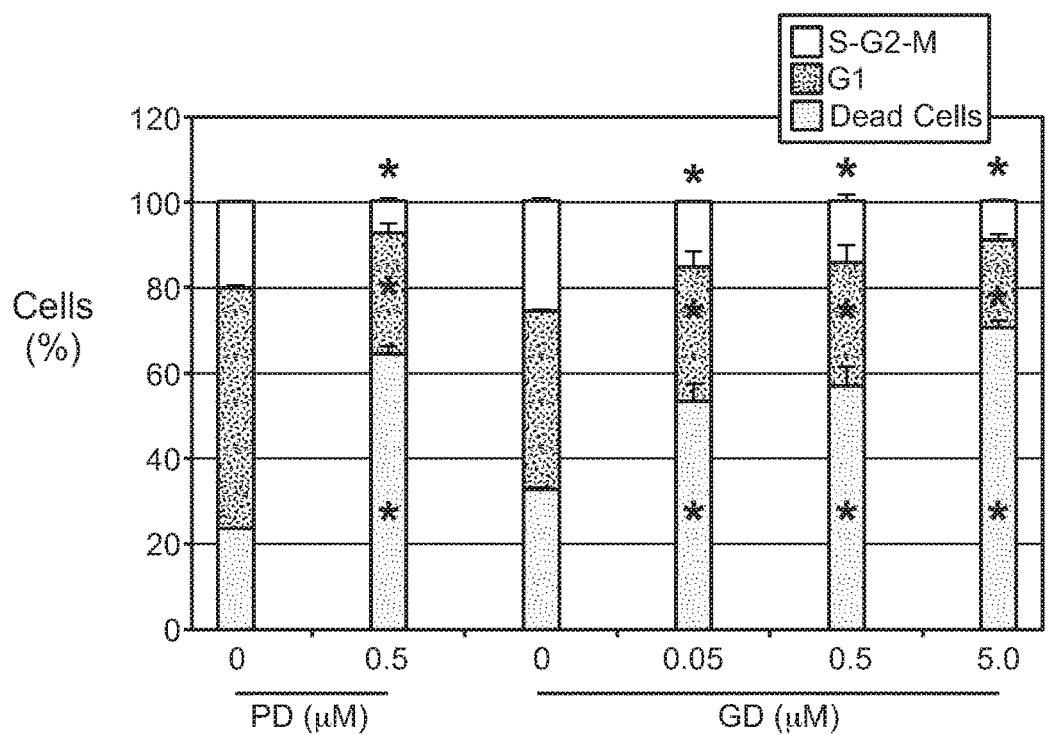
FIG. 3B is a histogram summarizing the cell cycle distribution of the PEER cell line in FIG. 3A. Data shown are mean±S.D. (n=6); *P<0.05 vs its vehicle controls, t-test.
Figure 3C:
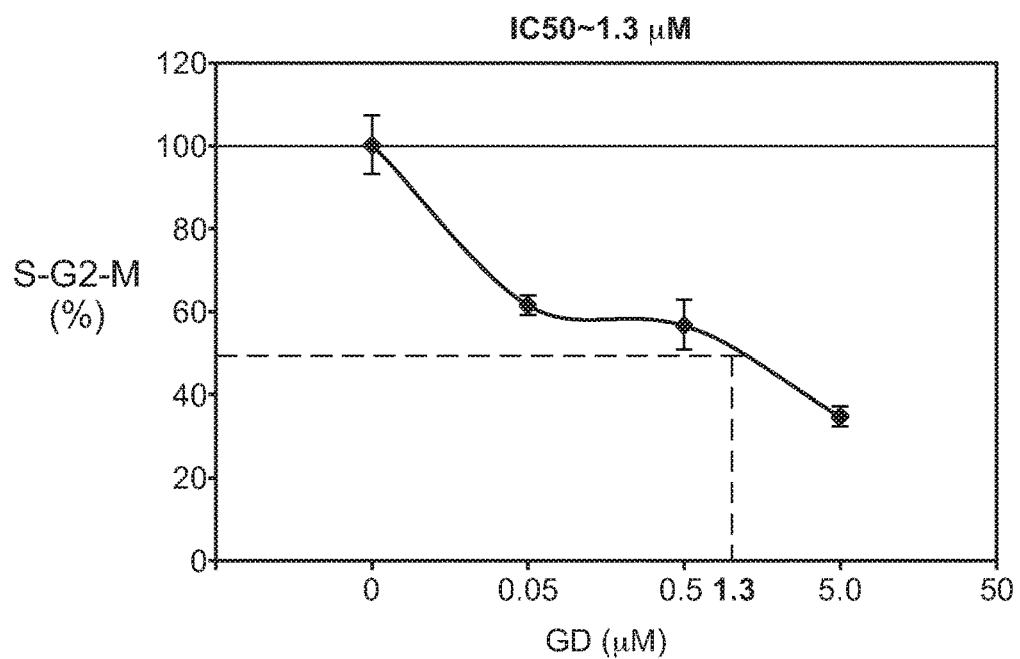
FIG. 3C is a chart showing the percentage of S-G2-M cells in FIG. 3B. IC50 for compound GD is ca. 1.3 µM.
Figure 4A:
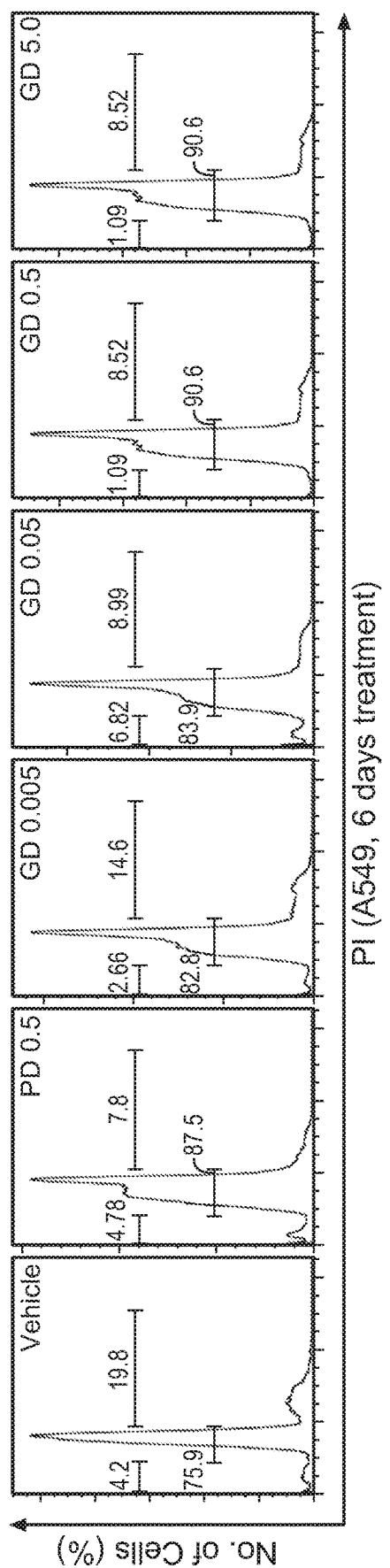
FIG. 4A is a series of charts showing representative cell cycle profiles of human lung cancer cell line A549 treated with a vehicle (V) (for palbociclib (PD) or compound GD), PD (0.5 µM), or compound GD at 0.005, 0.05, 0.5, and 5 µM for 6 days.
Figure 4B:
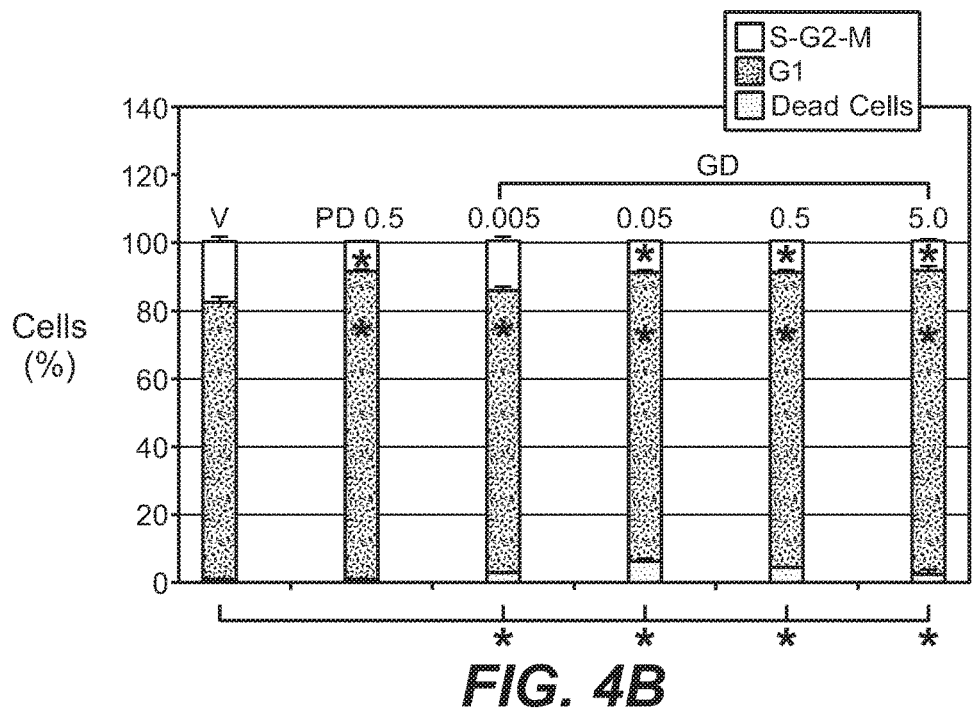
FIG. 4B is a histogram showing the cell cycle distribution of A549 cell line in FIG. 4A. Data shown are mean±S.D. (n=6); *P<0.05 vs its vehicle controls, t-test.
Figure 4C:
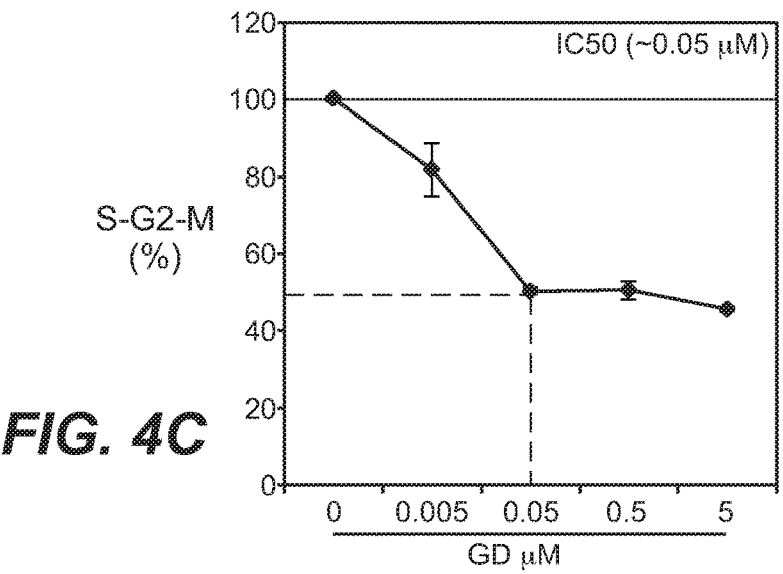
FIG. 4C is a chart showing the percentage of S-G2-M cells in FIG. 4B. IC50 for compound GD is ca. 0.05 µM.
Figure 4D:
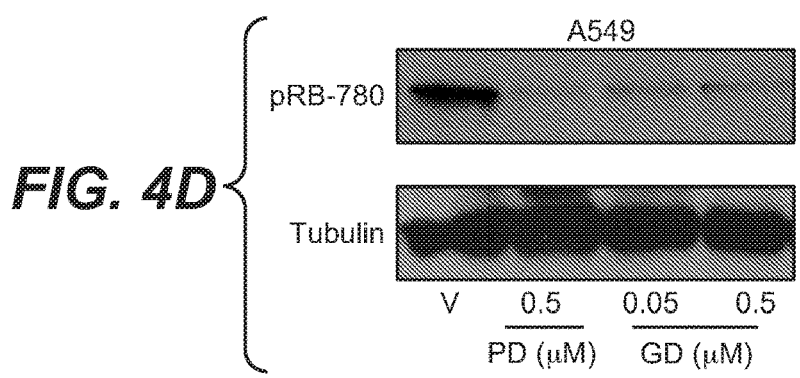
FIG. 4D is an image of representative immunoblots showing the levels of phosphorylated pRB at SER-780 in A549 cells following treatment with a vehicle, PD, or compound GD for 24 hours. Tubulin was used as a loading control.

HCl salt of 6-acetyl-5-methyl-2-((4-(piperazin-1-ylmethyl)thiazol-2-yl)amino)pyrido[2,3-d]pyrimidin-7(8H)-one (Compound GD) prepared in Example 1 was examined for its inhibitory activity in cancer cell lines and WT and CDK6$^{-/-}$ mouse embryonic fibroblasts (MEFs) and stromal vascular fractions (SVFs). MEFs and SVFs are enriched with mesenchymal stem cells (MSC) and pre-adipocytes which can differentiate into a variety of cell types, including adipocytes. Compared with ribociclib (LEE), compound GD efficiently suppresses growth of some leukemic cell lines with lower IC50, for instance, for leukemia cell lines HPBALL (FIGS. 1A-1E, IC50 for compound GD is ca. 4 µM, IC50 for LEE is ca. 12 µM). Compound GD also efficiently inhibits growth of other two T-ALL cell lines T-ALL1 (FIGS. 2A-2D) and PEER (FIGS. 3A-3C) with IC50 of ca. 1.1 µM and ca. 1.3 µM, respectively.

Figure 5A:
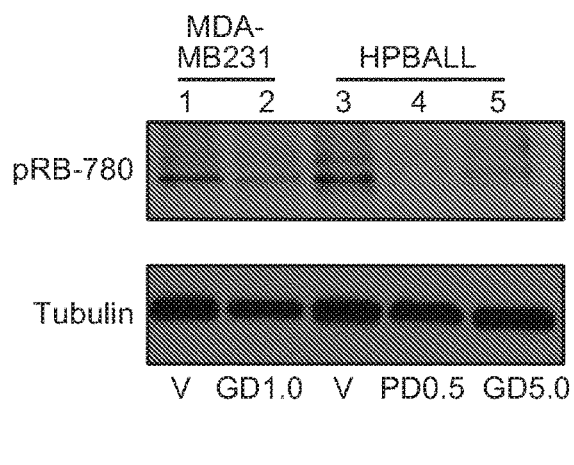
FIG. 5A is an image of a representative immunoblot showing the levels of phosphorylated pRB at SER-780 in MDA-MB231 and HPBALL cells following treatment of these cells with a vehicle, PD, or compound GD for 24 hours. Tubulin was used as loading control.
Figure 5B:
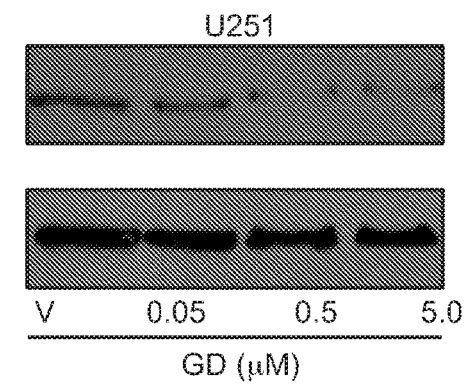
FIG. 5B is an image of a representative immunoblot showing the levels of phosphorylated pRB at SER-780 in U251 cells following treatment of these cells with a vehicle, PD, or compound GD for 24 hours. Tubulin was used as loading control.
Figure 5C:
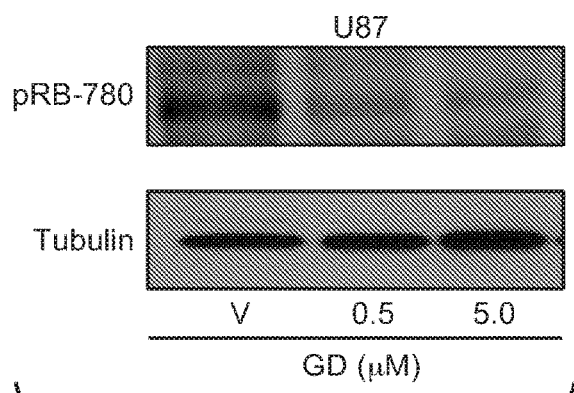
FIG. 5C is an image of a representative immunoblot showing the levels of phosphorylated pRB at SER-780 in U87 cells following treatment of these cells with a vehicle, PD, or compound GD for 24 hours. Tubulin was used as loading control.
Figure 5D:
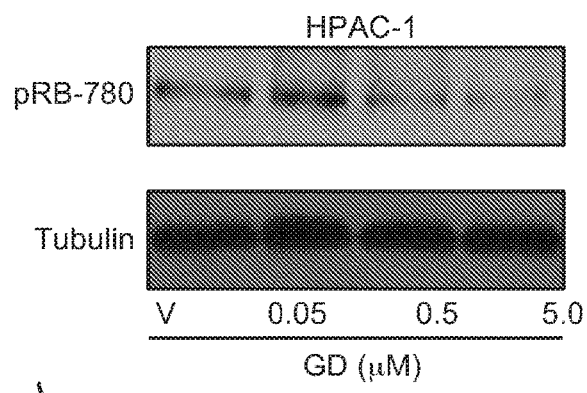
FIG. 5D is an image of a representative immunoblot showing the levels of phosphorylated pRB at SER-780 in HPAC-1 cells following treatment of these cells with a vehicle, PD, or compound GD for 24 hours. Tubulin was used as loading control.
Figure 5E:
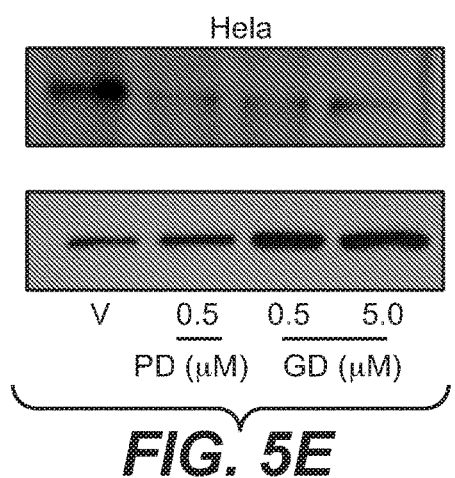
FIG. 5E is an image of a representative immunoblot showing the levels of phosphorylated pRB at SER-780 in HELA cells following treatment of these cells with a vehicle, PD, or compound GD for 24 hours. Tubulin was used as loading control.

In addition to T-ALL cell lines, compound GD also inhibits growth of other cancer cell lines, e.g., lung cancer cell line A549 (FIGS. 4A-4D). Compound GD also inhibits pRB phosphorylation of breast cancer cell line MDA-MB231 (FIG. 5A), glioblastoma cell lines U251 and U87 (FIGS. 5B and 5C), pancreas adenocarcinoma (HPAC-1) (FIG. 5D), and cervical cancer cell line (Hela cells, FIG. 5E).

Figure 6A:
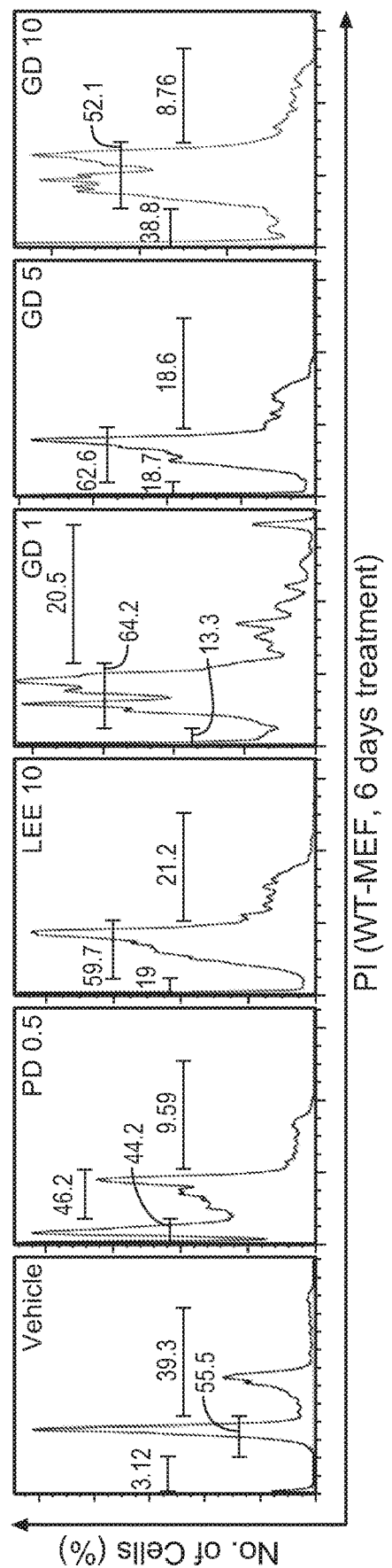
FIG. 6A is a series of charts showing representative cell cycle profiles of mouse WT-MEFs treated with a vehicle (V), PD (0.5 µM), LEE (10 µM), or compound GD at 1, 5, and 10 µM for 6 days.
Figure 6B:
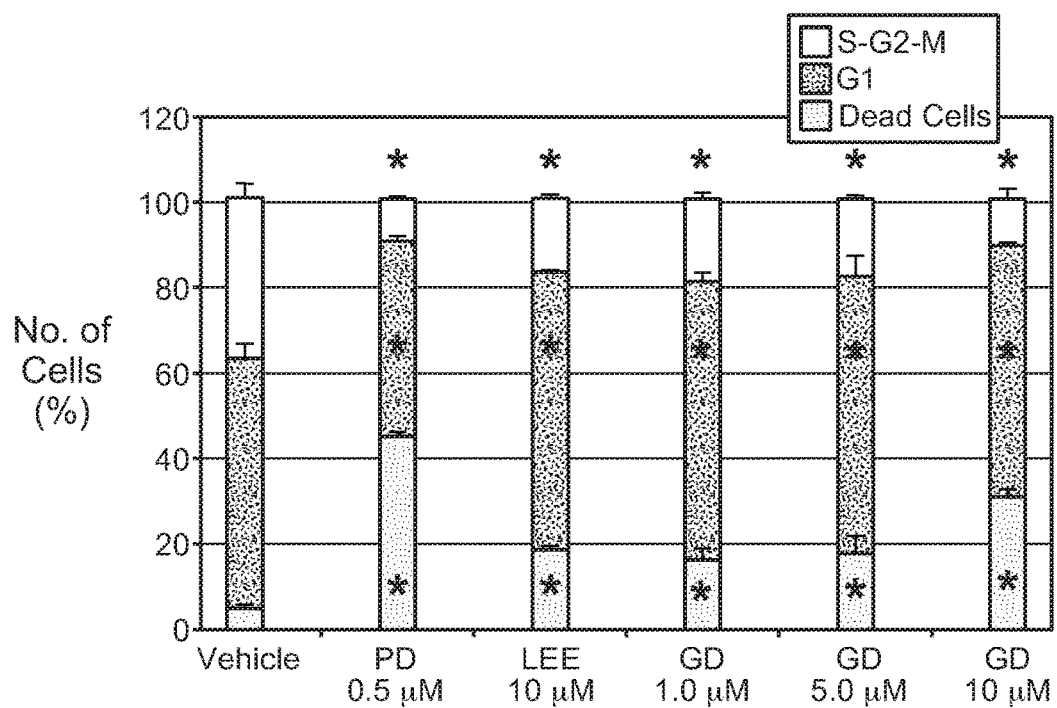
FIG. 6B is a histogram summarizing the cell cycle distribution in FIG. 6A. Data shown are mean±S.D. (n=6); *P<0.05 vs vehicle control, t-test.
Figure 6C:
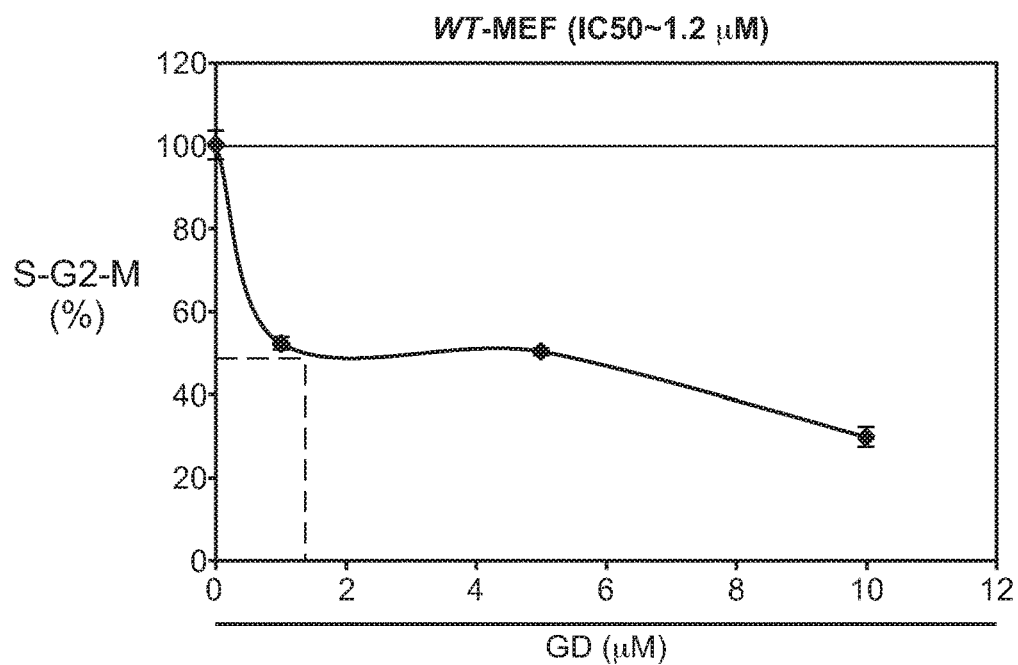
FIG. 6C is a chart showing the percentage of S-G2-M cells in FIG. 6B. IC50 for compound GD is ca. 1.2 µM.
Figure 6D:
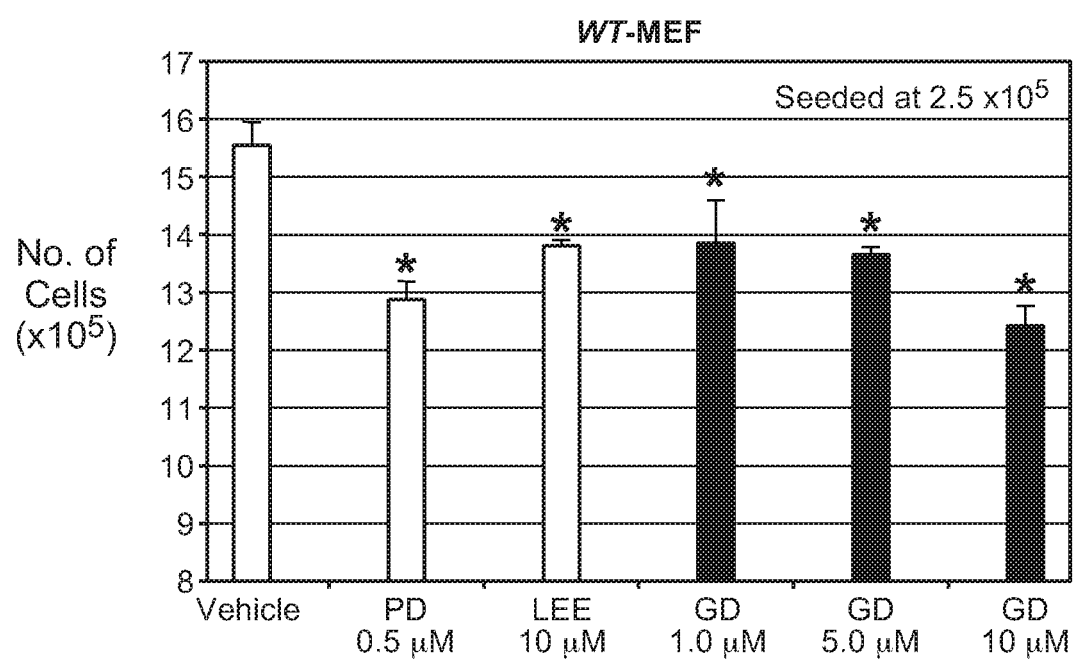
FIG. 6D is a bar graph summarizing the cell number of WT-MEFs treated with PD (0.5 µM), LEE (10 µM), or compound GD at varying doses for 6 days. Data shown are mean±S.D. (n=6); *P<0.05 vs vehicle control, t-test.
Figure 6E:
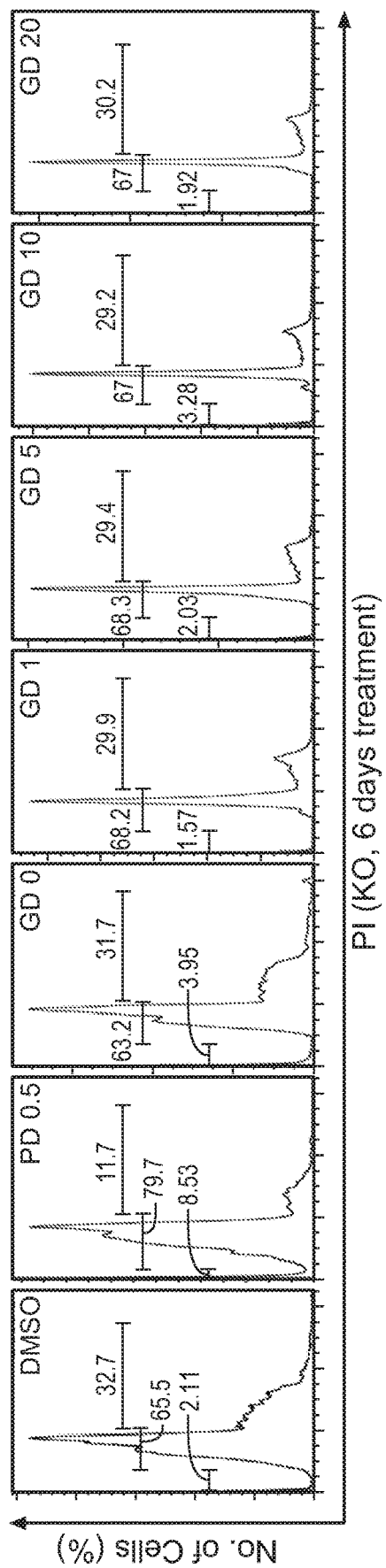
FIG. 6E is a series of charts showing representative cell cycle profiles of mouse KO-MEFs treated with a vehicle (V), PD (0.5 µM), or compound GD at 1, 5, 10, and 20 µM for 6 days.
Figure 6F:
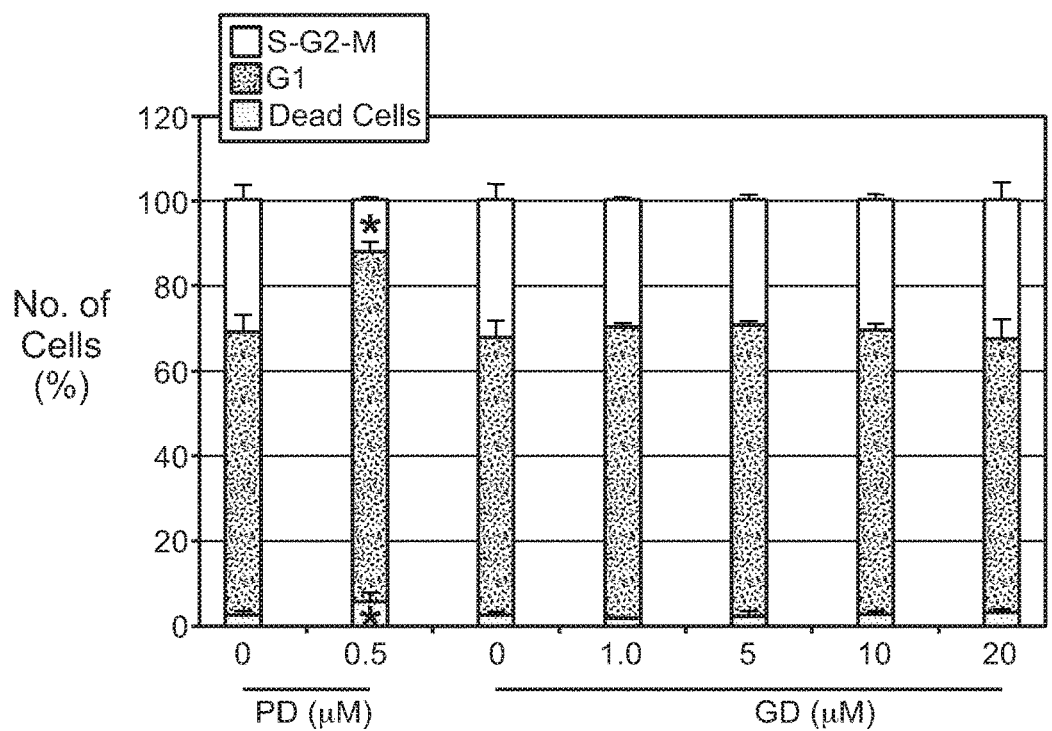
FIG. 6F is a histogram summarizing the cell cycle distribution in FIG. 6E. Data shown are mean±S.D. (n=6); *P<0.05 vs its vehicle control, t-test.
Figure 6G:
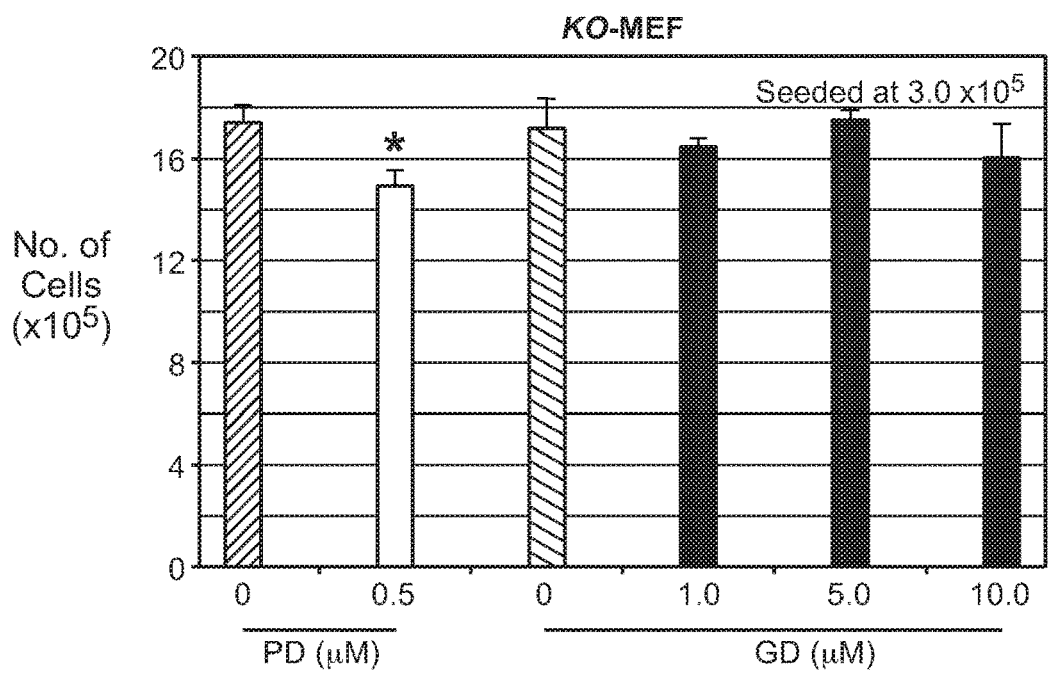
FIG. 6G is a bar graph summarizing the cell numbers of KO-MEFs treated with PD (0.5 µM) or compound GD at different doses for 6 days. Data shown are mean±S.D. (n=6); *P<0.05 vs its vehicle control, t-test.
Figure 7A:
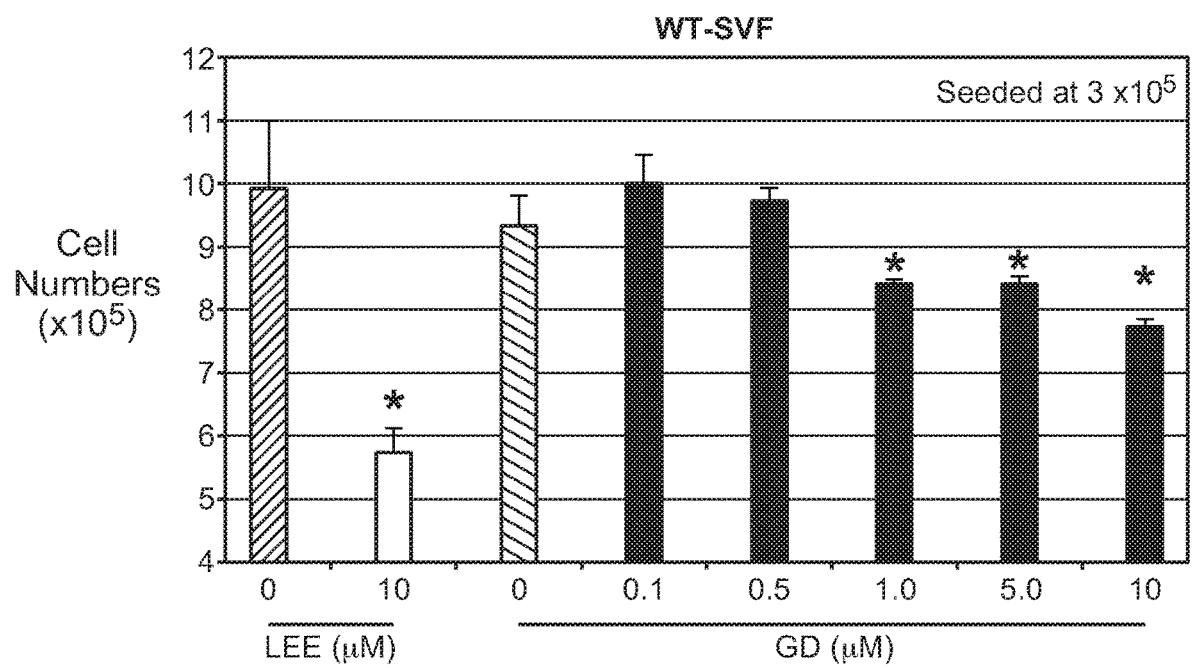
FIG. 7A is a bar graph showing the cell numbers of WT-SVFs treated with LEE (10 μM) or compound GD at 0.1, 0.5, 1.0, 5.0, and 10 μM for 6 days. Data shown are mean±S.D. (n=6); *P<0.05 vs its vehicle control, t-test.
Figure 7B:
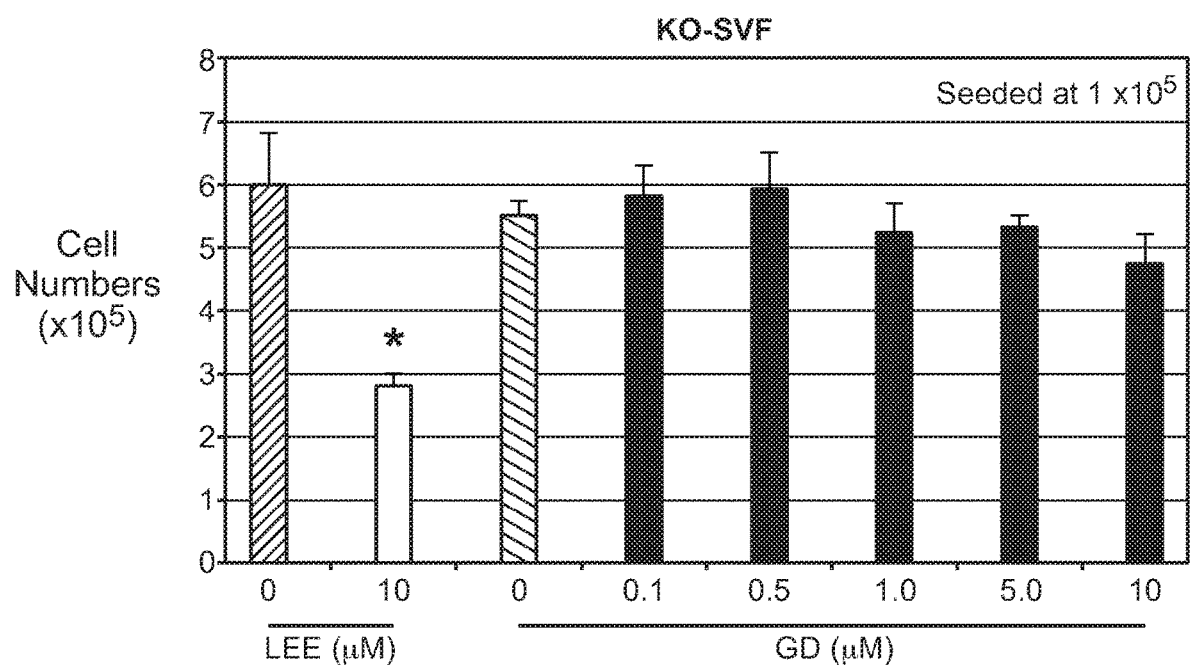
FIG. 7B is a bar graph showing the cell numbers of KO-SVFs treated with LEE (10 μM) or compound GD at 0.1, 0.5, 1.0, 5.0, and 10 μM for 6 days. Data shown are mean±S.D. (n=6); *P<0.05 vs its vehicle control, t-test.

Compound GD preferentially inhibits CDK6 over CDK4. As shown in FIGS. 6A-6G, GD inhibits proliferation of mouse WT-MEF in dose dependent manner with IC50 of ca. 1.2 µM (FIGS. 6A-6D), but has little effect on CDK6$^{-/-}$ MEFs (FIGS. 6E-6G). In contrast, palbociclib (PD) inhibited both WT and CDK6$^{-/-}$ MEFs (FIGS. 6B, 6D, 6F, and 6G). Compound GD inhibited proliferation of mouse WT SVFs in dose dependent manner (FIG. 7A) but had little effect on CDK6$^{-/-}$ SVFs (FIG. 7B). In contrast, PD inhibited cell proliferation of both WT and CDK6$^{-/-}$ SVFs (FIGS. 7A and 7B). These results indicate that compound GD inhibits cell cycle by preferentially targeting CDK6. Compound GD also has a reduced effect on cell viability relative to PD (FIG. 6B, PD 0.5 µM and GD 10 µM), as the fractions of dead cell from cells treated with compound GD (10 µM) is smaller than that from cells treated with PD (0.5 µM).

Figure 8A:
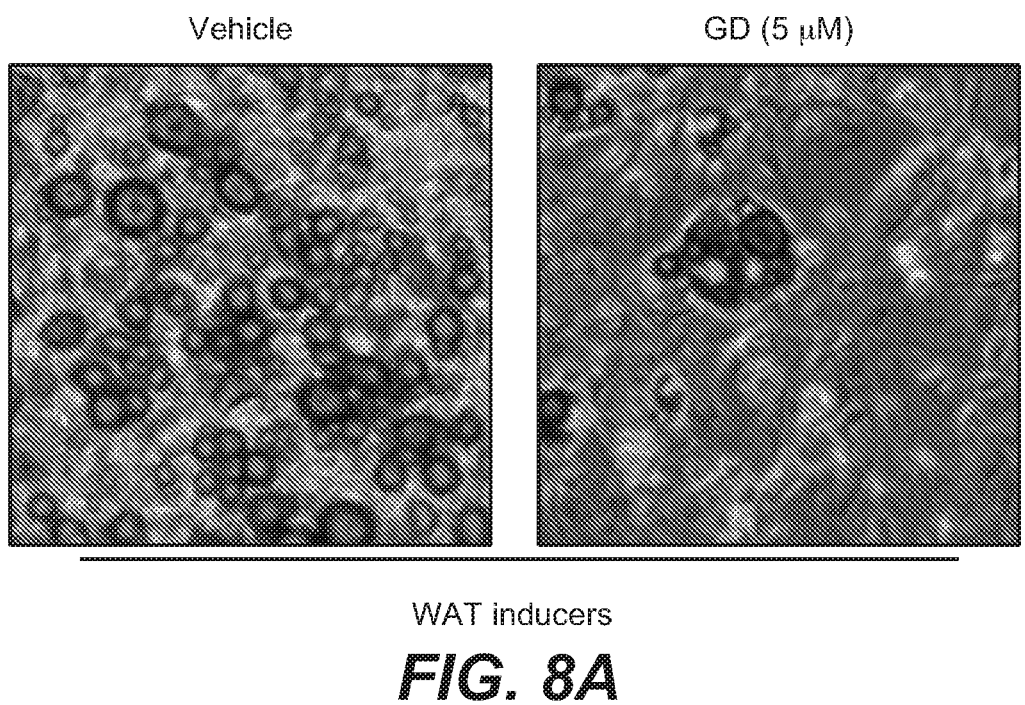
FIG. 8A is an image of Oil Red O staining of differentiated SVF cells treated with a vehicle or compound GD (5 μM) in the presence of white adipose tissue (WAT) inducers. Scale bar: 100 μM
Figure 8B:
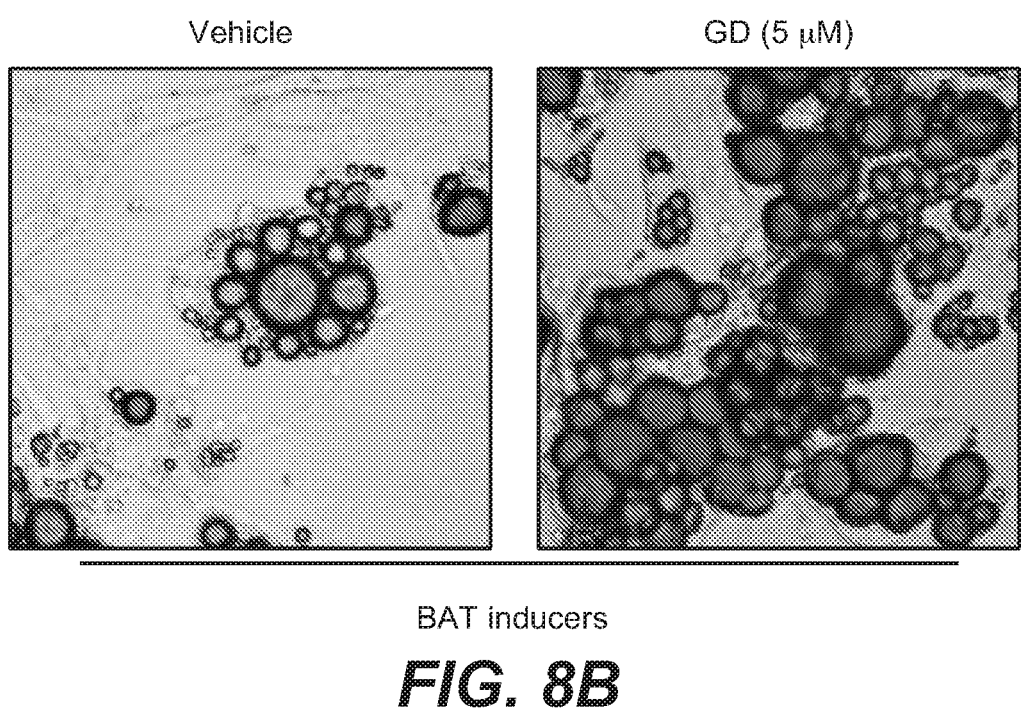
FIG. 8B is an image of Oil Red O staining of differentiated SVF cells treated with a vehicle or compound GD (5 μM) in the presence of brown adipose tissue (BAT) inducers. Scale bar: 100 μM
Figure 8C:
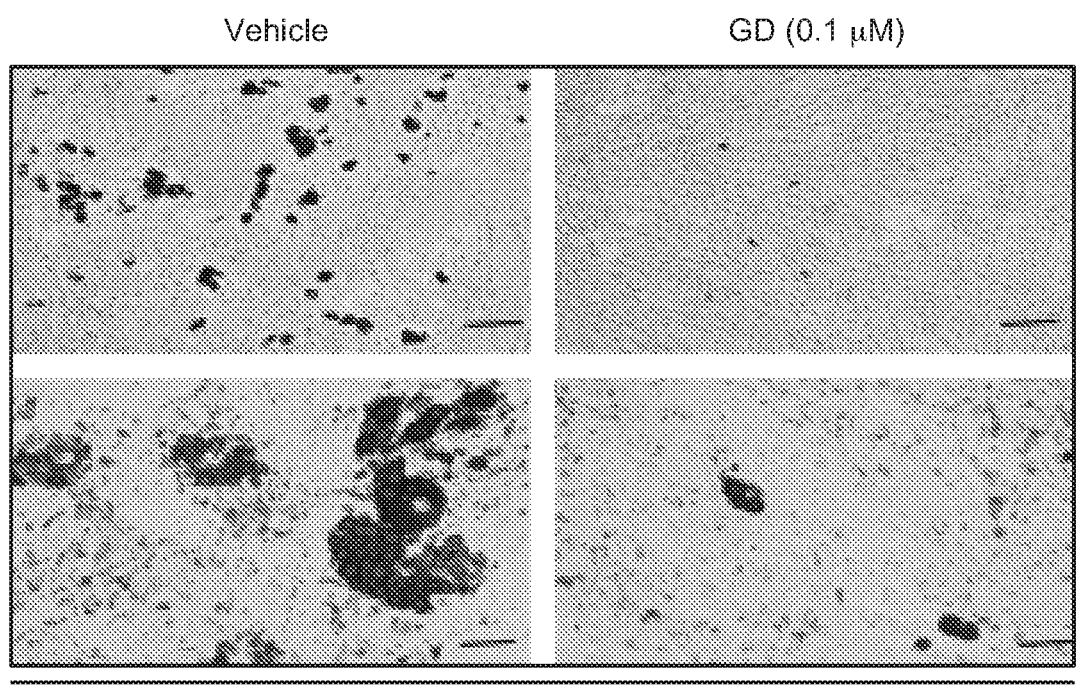
FIG. 8C is an image of Oil Red O staining of differentiated SVF cells treated with a vehicle or compound GD (0.1 μM) in the presence of white adipose tissue (WAT) inducers. Scale bar: 400 μM for the top 2 images, and 100 μM for the bottom two images.

Finally, inhibition of CDK6 inhibited white adipocyte formation (FIG. 8A (5 µM) and FIG. 8C (0.1 µM); the dark cells are white adipocytes, which decreased in number upon GD treatment relative to vehicle control), but induced beige cell formation (FIG. 8B, the dark cells are beige cells. Beige cells are associated with protection against obesity and metabolic syndrome (WO 2017/161253). Accordingly, compound GD and related compounds of the invention can be used for treating obesity and related metabolic diseases.

Together, these results suggest that compound GD is a more specific CDK6 inhibitor than palbociclib (PD) or ribociclib (LEE) and is therefore safer for use in treating subjects having cancer (e.g., T-cell acute lymphoblastic leukemia) or a metabolic disease (e.g., obesity or type II diabetes).

Table 2 lists the results for incubation of compound GD with various cell lines.

TABLE 2

| Cancer Cell Line | Experimental Procedure | Compound GD Efficacy |
|---|---|---|
| Leukemic cells: HPBALL, TALL1, PEER | PI Staining, and cell number counting | Efficacious |
| Cervical Cancer: Hela | WB: P-RB-780 | Efficacious |
| Lung Cancer: A549 | WB: P-RB-795, PI staining | Efficacious |
| Breast Cancer: MCF-7 | PI staining and WB: P-RB-780 | No |
| MDA-MB231 | PI staining and WB: P-RB-780 | Efficacious |
| Prostate Cancer: PC-3, DU145 | WB: P-RB-780 | No |
| Brain Tumor: U87 human primary glioblastoma cell line | WB: P-RB-780 | Efficacious |
| Brain Tumor: U251 | WB: P-RB-780 | Efficacious |
| Pancreas Cancer: HPAC | WB and PI staining | Efficacious |

Table 2: Experimental Procedures: sensitivity to CDK6 kinase activity inhibition was tested by incubating different cell lines in the presence of CDK6 inhibitor GD007/PBS for either 24 hours for detecting the status of pRB-780 phosphorylation, or 5 days for determining the effect of GD007 on cell proliferation. (1) By immunoblotting (WB), we will detect phospho-pRB-S$^{780}$, one of the substrates of CDK6 kinase; (2) By using FACS analysis, we will stain treated cells with Propidium Iodide (PI), a commonly used fluorescent intercalator, to measure the subpopulation of cell cycle to reveal any impact of CDK6 inhibition on cell proliferation; (3) cell numbers will be counted using hemocytometer.

Example 3

Figure 9A:
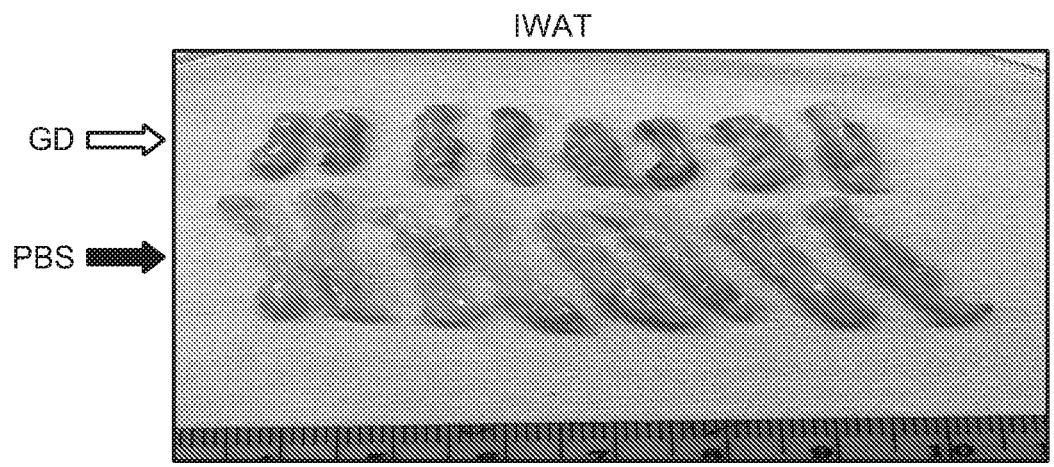
FIGS. 9A-9D show the effects of GD on fat pad mass and body weight, with FIGS. 9A-9C showing reduced fat mass in mice treated with CDK6 inhibitor GD.
Figure 9B:
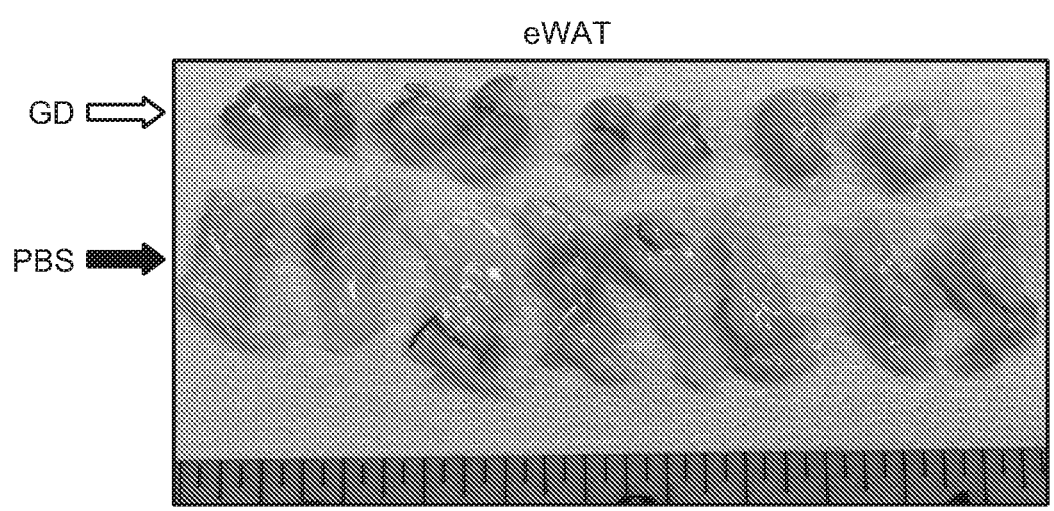
Figure 9C:
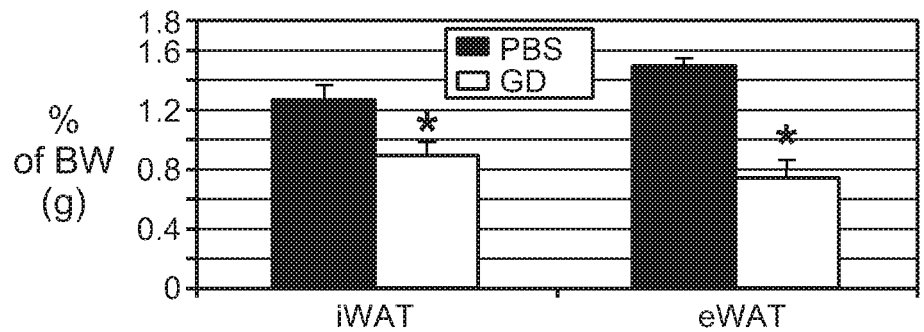
Figure 9D:
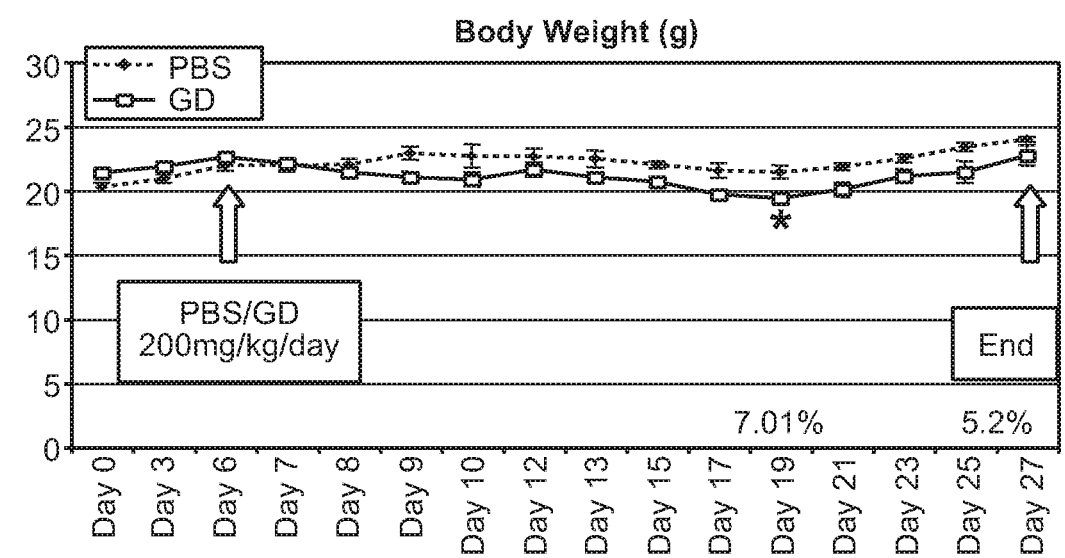

Inhibition of CDK6 Kinase Activity by GD007 (GD) Leads to Reduced White Fat Mass To investigate if inhibition of CDK6 kinase activity by GD alters the metabolic physiology of mice, we subjected WT (B6) mice to GD at 6-weeks-old to PBS/GD at dose of 200 mg/kg/day for 21-days (Kwapisz, Breast Cancer Res. Treat. 166:41-54, 2017), comparable with current use with CDK6 inhibitors in animal experiments (Rader et al., Clin. Cancer Res. 19:6173-6182, 2013) and current clinical use of CDK6 inhibitors in breast cancer (Kwapisz, supra). We observed dramatically and significantly decreased fat pad mass (FIGS. 9A-9C; ~1.42-fold reduction for iWAT, and ~2.0-fold reduction for eWAT) in GD-treated mice, as compared to those in PBS-treated mice. In contrast, the body weight of mice treated with GD displayed much less reduction under normal chow diet (NCD; FIG. 9D). The most significant reduction (7.1% reduction compared to PBS treated mice) in body weight was observed at ~2 weeks post treatment. These data show that the CDK6 specific inhibitor had potent effects on reducing fat pad mass without significantly reducing lean mass, showing a highly attractive pharmacological intervention for obesity and related T2D.

Example 4

GD Inhibited Growth of Established Lung Cancer in a Xenograft Mouse Model

We examined the therapeutic efficacy of GD against A549 (lung cancer cells) xenograft tumors. A549 cells ($3\times10^5$ per side in 100 µl of 50% Matrigel) were inoculated ectopically in female Nod/Scid mice on both sides. When tumor sizes reached ~50 mm$^3$, animals were divided into 2 groups (n=4 mice per group), and treated with PBS or GD at dose of 200 mg/kg/day over a 21-day period (Kwapisz, supra).

Tumor sizes were measured with standard calipers every day and tumor volumes were calculated using standard methods (caliper measurements are commonly collected along the longest two dimensions of the tumor x/y plane only, with the z-axis dimension assumed to be the same as the shortest dimension) (Tomayko et al., *Cancer Chemother. Pharmacol.* 24:148-154, 1989). Weekly body weights were measured at designed times. At the end of the experiments, all of the tumors were isolated from the mice and weighed.

Figure 10A:
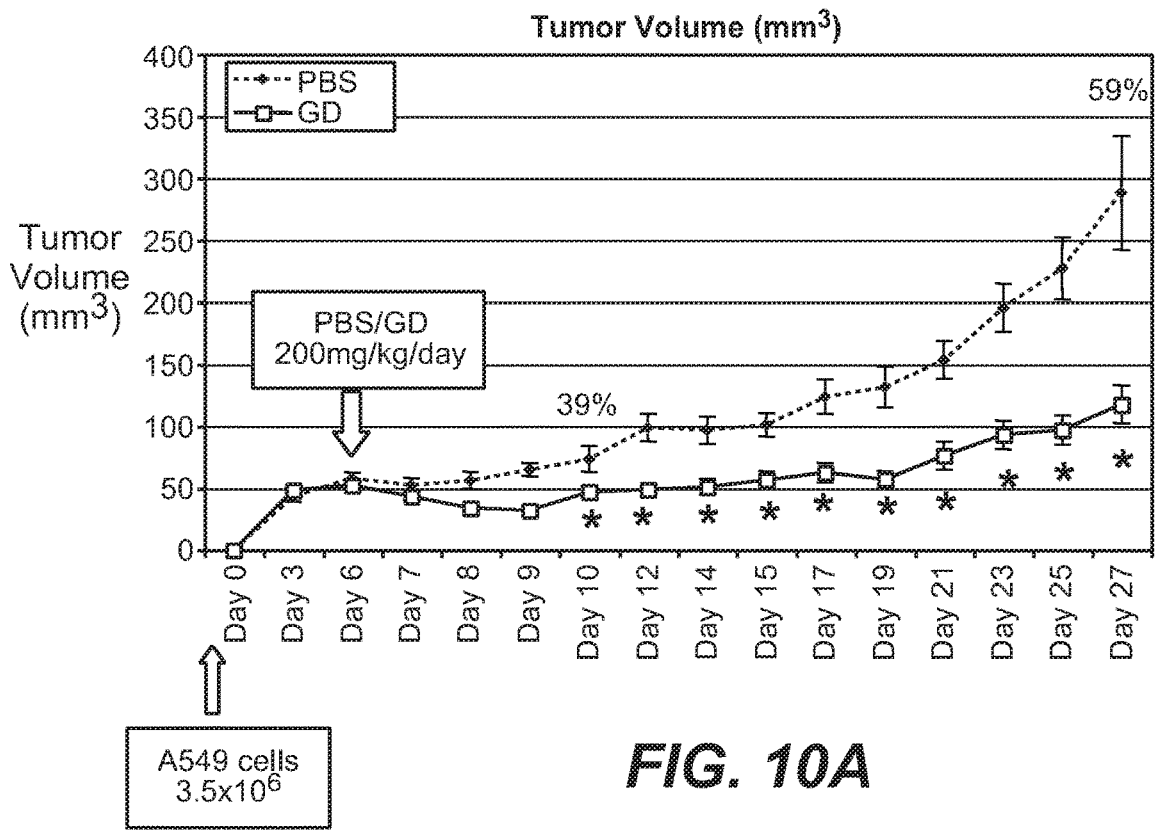
FIGS. 10A-10D show that GD inhibited growth of established lung cancer in a xenograft mouse model.
Figure 10B:
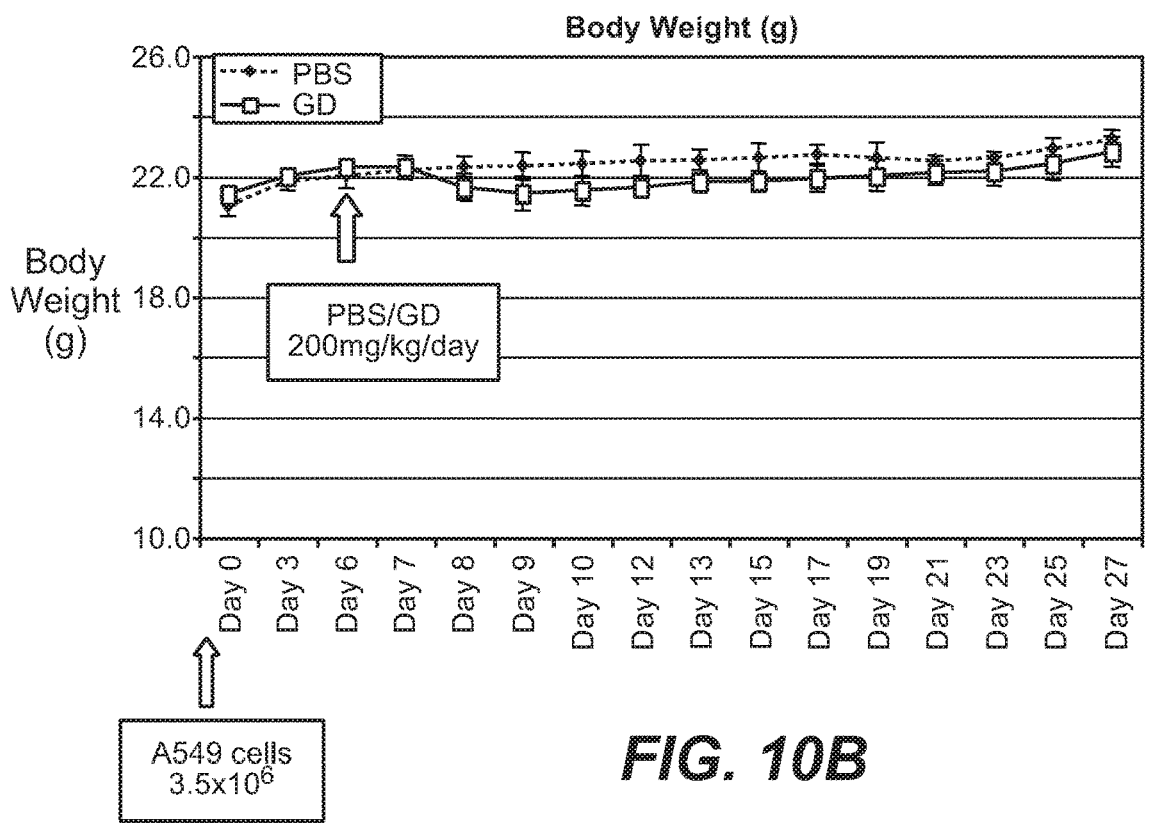
Figure 10C:
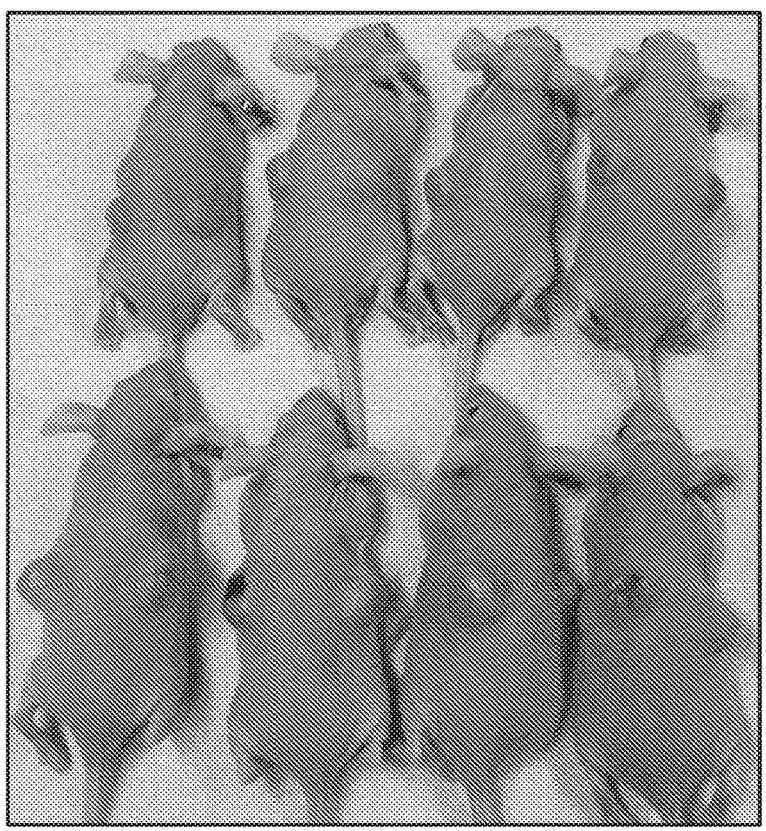
Figure 10D:
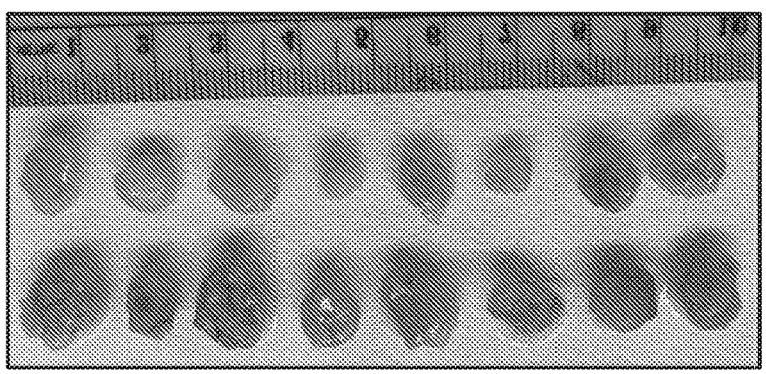
Figure 10E:
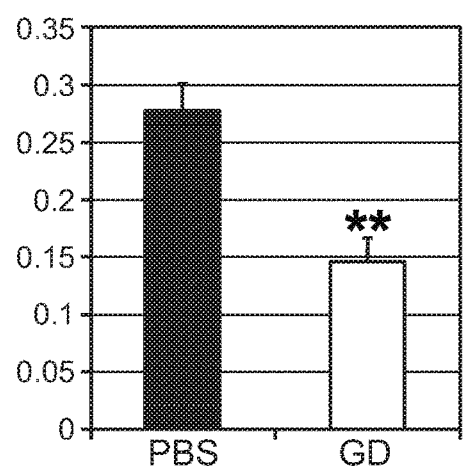
FIG. 10E is a graph showing decreased tumor weights from tumor bearing mice treated with GD. Data shown are mean±S.D. (n=8 for each group), *p<0.05, t-test, GD vs PBS.

Consistent with the in vitro analysis, GD inhibited growth of established lung cancer in the xenograft mouse model, as shown by reduced tumor volumes (FIG. 10A) and tumor weights (FIGS. 10D-10E). By contrast, despite different tumor masses, mice had similar body weights between GD and PBS treated groups (FIG. 10B), showing again that GD does not significantly reduce lean mass.

In summary, inhibition of CDK6 kinase activity by GD leads to reduced white fat and tumor masses.

Other Embodiments

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention. It is to be understood that each of the additional features defined the dependent claims apply to the compound specified in prior claims (e.g., the compound of formula I) or a pharmaceutical salt thereof.

Some embodiments of the invention are within the scope of the following numbered paragraphs.

1. A compound of formula (I):

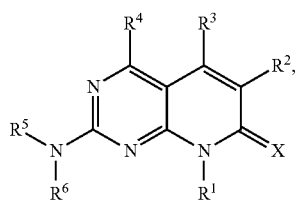

or a pharmaceutically acceptable salt thereof,
wherein
X is O or S;
R$^1$ is hydrogen, an optionally substituted C$_{1-6}$ alkyl, or an optionally substituted C$_{3-8}$ cycloalkyl;
each of R$^2$, R$^3$, and R$^4$ is independently hydrogen, halo, or an optionally substituted C$_{1-6}$ alkyl;
R$^5$ is a substituted C$_3$ heteroaryl; and
R$^6$ is hydrogen or an optionally substituted C$_{1-6}$ alkyl.

2. The compound of paragraph 1, wherein X is O.
3. The compound of paragraph 1 or 2, wherein R$^1$ is hydrogen.
4. The compound of any one of paragraphs 1 to 3, wherein R$^2$ is an optionally substituted C$_{1-6}$ alkyl.
5. The compound of paragraph 4, wherein R$^2$ is an optionally substituted C$_{1-6}$ alkanoyl.
6. The compound of any one of paragraphs 1 to 5, wherein R$^3$ is an optionally substituted C$_{1-6}$ alkyl.
7. The compound of any one of paragraphs 1 to 6, wherein R$^4$ is hydrogen.
8. The compound of any one of paragraphs 1 to 7, wherein R$^5$ is a substituted thiazolyl or substituted oxazolyl.
9. The compound of paragraph 8, wherein R$^5$ is thiazolyl or oxazolyl substituted with an optionally substituted C$_{1-9}$ heterocyclyl C$_{1-6}$ alkyl.
10. The compound of paragraph 9, wherein R$^5$ is a group of formula:

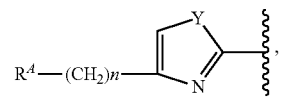

wherein
n is an integer from 0 to 6;
Y is S or O; and
R$^A$ is an optionally substituted C$_{1-9}$ heterocyclyl.
11. The compound of paragraph 10, wherein n is 1.
12. The compound of paragraph 10 or 11, wherein R$^A$ is N-piperazinyl.
13. The compound of any one of paragraphs 1 to 12, wherein R$^6$ is hydrogen.
14. A compound of the following structure:

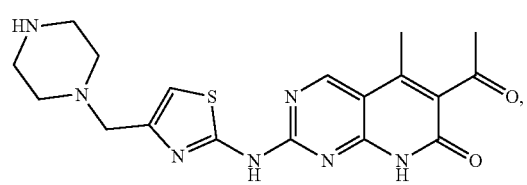 [SMILES: CC(=O)c1c(C)c2cnc(Nc3nc(CN4CCNCC4)cs3)nc2[nH]c1=O]

or a pharmaceutically acceptable salt thereof.

15. A pharmaceutical composition comprising the compound of any one of paragraphs 1 to 14 and a pharmaceutically acceptable excipient.
16. A method of treating a subject having a cancer, the method comprising administering to the subject in need thereof an effective amount of the compound of any one of paragraphs 1 to 14 or the pharmaceutical composition of paragraph 15.
17. The method of paragraph 16, wherein the cancer is leukemia, lung cancer, brain tumor, breast cancer, cervical cancer, or pancreatic cancer.
18. A method of treating a subject having a metabolic disease, the method comprising administering to the subject in need thereof an effective amount of the compound of any one of paragraphs 1 to 14 or the pharmaceutical composition of paragraph 15.
19. The method of paragraph 18, wherein the metabolic disease is obesity, type II diabetes, metabolic syndrome, elevated blood pressure, a cardiovascular disease, elevated fasting plasma glucose, or a high level of serum triglycerides.

20. The method of any one of paragraphs 16 to 19, wherein the subject is human.

21. A method of inducing cell death in a cancer cell, the method comprising contacting the cancer cell with the compound of any one of paragraphs 1 to 14.

22. The method of paragraph 21, wherein the cancer cell is a leukemic cell, cervical cancer cell, lung cancer cell, brain tumor cell, breast cancer cell, or pancreatic cancer cell.

Other embodiments are within the scope of the claims.

What is claimed is:

1. A compound of the following structure:

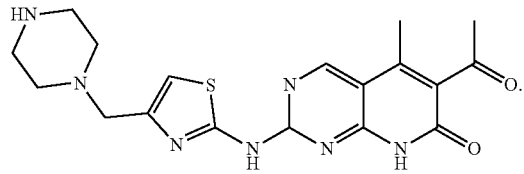

or a pharmaceutically acceptable salt thereof.

2. A pharmaceutical composition comprising the compound of claim 1 and a pharmaceutically acceptable excipient.

* * * * *